United States Patent [19]
Frei et al.

[11] Patent Number: 5,516,806
[45] Date of Patent: May 14, 1996

[54] ORNITHINE DECARBOXYLASE INHIBITING CYCLIC AMINOOXY COMPOUNDS

[75] Inventors: Jörg Frei, Hölstein; Jaroslav Stanek, Arlesheim, both of Switzerland

[73] Assignee: Ciba-Geigy Corporation, Tarrytown, N.Y.

[21] Appl. No.: 351,337

[22] PCT Filed: Apr. 2, 1994

[86] PCT No.: PCT/EP94/01035

§ 371 Date: Dec. 12, 1994

§ 102(e) Date: Dec. 12, 1994

[87] PCT Pub. No.: WO94/24093

PCT Pub. Date: Oct. 27, 1994

[30] Foreign Application Priority Data

Apr. 13, 1993 [CH] Switzerland ............... 1128/93

[51] Int. Cl.⁶ ............ A61K 31/13; C07C 239/10
[52] U.S. Cl. ............ 514/645; 564/300; 514/895
[58] Field of Search ............ 514/645, 895; 564/300, 306

[56] References Cited

U.S. PATENT DOCUMENTS

| | | | |
|---|---|---|---|
| 3,192,110 | 6/1965 | Biel et al. | 167/65 |
| 4,425,340 | 1/1984 | Teraji et al. | 514/202 |
| 4,472,194 | 9/1984 | Van Assche et al. | 71/121 |
| 5,254,717 | 10/1993 | Grammenos et al. | 560/35 |

FOREIGN PATENT DOCUMENTS 0291957  11/1988  European Pat. Off. .
253817   2/1984  Japan .

OTHER PUBLICATIONS

AU 44711/89 (text) english equivelant of 0–369–944 (1989).

AU 10177/92 (text) english equivelant of 0–495–750 (1992).

92–286002/27 Derwent Abstract EP 499823 (see U.S. 5,254,717) (1992).

92–218598/35 Derwent Abstract EP 492366 (1992).

Stanek et al "2–Substituted 3–(Aminooxy) Propanamines as Inhibitors of Ornithine Decaeboxylase: Synthesis and Biological Activity" J. Med. Chem. vol. 35 (1992) pp. 1339–1344.

Moyano et al "Inhibition of Ornithine Decarboxylase by the Isomers of 1,4 Dimethylputrescine" J. Med. Chem. vol. 33, (1990) 1969–1974.

Primary Examiner—Brian M. Burn
Attorney, Agent, or Firm—Irving M. Fishman; Karen G. Kaiser

[57] ABSTRACT

Compounds of formula (I): $H_2N-(CH_2)_n-A-(CH_2)_m-O-NH_2$ and salts thereof are described in which the radical A is $C_3-C_6$ cycloalkylene; n is 0 or 1 and, independently thereof, m is 0 or 1; with the provisos that a) the distance between the aminooxy radical $H_2N-O-$ and the amino group $-NH_2$ is at least 3 and not more than 4 carbon atoms and that b) the two radicals $H_2N-(CH_2)_n-$ and $-(CH_2)_m-O-NH_2$ are not bonded to the same ring carbon of A. The compounds of formula (I) and their salts are ornithine decarboxylase inhibitors.

25 Claims, No Drawings

ORNITHINE DECARBOXYLASE INHIBITING CYCLIC AMINOOXY COMPOUNDS

This application is a 371 of PCT/EP94/01035, filed Apr. 2, 1994.

The present invention relates to novel pharmaceutically active cyclic aminooxy compounds, processes for the preparation of these compounds, pharmaceutical compositions comprising these compounds, these compounds for use in a prophylactic, therapeutic or diagnostic method for the treatment of the human or animal body, and the use of these compounds for the prophylactic or therapeutic treatment of the human or animal body and for the preparation of pharmaceutical compositions.

According to the current state of knowledge, participation of the polyamines spermidine and spermine and the diamine putrescine in regulation of growth processes is to be assumed.

A number of cell functions can be favourably influenced by inhibition of polyamine biosynthesis.

The enzyme ornithine decarboxylase (ODC) is one of the key enzymes of polyamine biosynthesis. A reduction in the activity of ODC leads to a reduced polyamine biosynthesis and therefore to reduced polyamine levels in the cell. If inhibition of the activity of this enzyme by ODC inhibitors is achieved, the polyamine concentration in mammalian cells (including human cells) can be influenced, i.e. lowered, with the aid of such ODC inhibitors.

In mammalian cells, ODC catalyses the synthesis of putrescine, a diamine which at the same time is also an intermediate in polyamine biosynthesis.

It has now been found, surprisingly, that the compounds of the present invention which have a cyclic central constituent have advantageous pharmacological properties.

The compounds according to the invention are those of the formula I

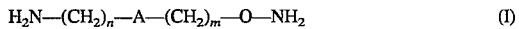

in which the radical A is $C_3$–$C_6$cycloalkylene;

n is 0 or 1 and, independently thereof, m is 0 or 1;

with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, and salts thereof.

The compounds of the present invention can exist as mixtures of cis and trans isomers or, preferably, as pure cis or pure trans isomers; if asymmetric carbon atoms are present (i.e. if A is other than 1,4-cyclohexylene or 1,3-cyclobutylene), these carbon atoms can be in the (R), (S) or (R,S) configuration, independently of one another. In mixtures of cis and trans isomers, in each case both or only one of the optical antipodes of the cis and of the trans isomer can be present. Pure cis or trans isomers, which can exist as pure enantiomers or enantiomer mixtures, for example as racemic mixtures, in particular as pure enantiomers, are preferred.

The terms and general expressions used in the description of the present invention are preferably defined as follows:

$C_3$–$C_6$Cycloalkylene A, in which the two radicals $H_2N$—$(CH_2)_n$— and —$(CH_2)_m$—O—$NH_2$ are not bonded to the same ring carbon atom, is the bivalent radical of a cyclic hydrocarbon and is chosen from 1,2-cyclopropylene; 1,2- or 1,3-cyclobutylene; 1,2- or 1,3-cyclopentylene; and 1,2-, 1,3-or 1,4-cyclohexylene; 1,2-cyclopropylene, 1,3-cyclobutylene, 1,3-cyclopentylene or 1,3- or 1,4-cyclohexylene is preferred.

The distance between the aminooxy radical $H_2N$—O— and the amino group —$NH_2$ of at least 3 and not more than 4 carbon atoms is defined such that the shortest connection between the radical $H_2N$—$(CH_2)_n$— and the radical —$(CH_2)_m$—O—$NH_2$ is to be included when counting the carbon atoms in ring A. The numerical values; of n and m are to be chosen accordingly within the context of proviso a); preferably, n is 0 and m is 0 or 1.

Salts of compounds according to the invention are acid addition salts, in particular pharmaceutically acceptable acid addition salts, i.e. those acid addition salts which do not have a troublesome toxicity in the particular dosage to be used, for example salts with inorganic acids, such as hydrochloric acid, sulfuric acid or phosphoric acid, or with suitable organic carboxylic or sulfonic acids, for example acetic acid, octanoic acid, succinic acid, adipic acid, fumaric acid, maleic acid, hydroxymaleic acid, propionic acid, lactic acid, malic acid, citric acid, salicylic acid, p-aminosalicylic acid, ascorbic acid, oxalic acid, benzenesulfonic acid, 1,5-naphthalenedisulfonic acid, methanesulfonic acid or 1,2-ethanedisulfonic acid, with N-cyclohexylsulfamic acid, or, for example, with amino acids, such as glutamic acid or aspartic acid. Mono- or disalts can be formed, depending on the basicity of the basic groups present.

Pharmaceutically unsuitable salts, for example picrates or perchlorates, can also be used for isolation or purification. Only pharmaceutically acceptable salts are used therapeutically, and are therefore preferred.

The compounds according to the invention have useful, in particular pharmacologically usable, properties. Surprisingly, it has been found that the compounds of the formula I have a particularly potent, specific inhibiting action on the enzyme ornithine decarboxylase (ODC), which is selective with respect to diamine oxidase (DAO). They are a novel class of ODC inhibitors.

ODC plays an important role as a key enzyme in polyamine biosynthesis, which proceeds in practically all cells of mammals, including humans. The polyamine concentration in the cell is regulated by ODC. Inhibition of the enzyme ODC results in a reduction in the polyamine concentration. Since a reduction in the polyamine concentration causes inhibition of cell growth, it is possible to inhibit the growth of eucaryotic and also of procaryotic cells, in particular of rapidly or uncontrollably growing cells, and even to destroy cells or inhibit the onset of cell differentiation, by administration of ODC-inhibiting substances.

The inhibition of the enzyme ODC can be demonstrated, for example, by the method of J. E. Seely and A. E. Pegg, Ornithine Decarboxylase (Mouse Kidney), pages 158–161, in H. Tabor and C. White-Tabor (editors): Methods in Enzymology, Volume 94: Polyamines, Academic Press, New York 1983. If ODC from rat liver is used in this test (isolation: Hayashi, S.-I. and Kameji, T., same volume, pages 154–158), $IC_{50}$ values in the micromolar region, down to about 0.01 μM, preferably between about 0.01 and 10 μM, for example between about 0.02 and about 7.2 μM, are obtained for the compounds of the formula I. $IC_{50}$ is the concentration of the inhibitor at which the ODC activity is 50% of that of a control without the inhibitor.

As ODC inhibitors, the compounds of the formula I have antiproliferative properties, which can be demonstrated, for example, by demonstrating the inhibiting action on the growth of human T24 bladder carcinoma cells. The demonstration is effected by incubating these cells in "Eagle's minimal essential medium", to which 5% (v/v) of foetal calf serum has been added, in air in a humidified incubator at 37° C. and 5 percent by volume of $CO_2$. The carcinoma cells (1000–1500) are transinoculated into 96-depression microlitre plates and incubated overnight under the conditions mentioned. The test substance is added in serial dilutions on day 1. The plates are incubated under the conditions mentioned for 5 days. During this period of time, the control cultures pass through at least 4 cell divisions. After the incubation, the cells are fixed with 3.3% (weight/volume= w/v) aqueous glutaraldehyde solution, washed with water and dyed with 0.05% (w/v) aqueous methylene blue solution. After washing, the dye is eluted with 3% (w/v) aqueous hydrochloric acid. Thereafter, the optical density (OD) per depression, which is directly proportional to the number of cells, is measured with a photometer (Titertek multiskan) at 665 nm. The $IC_{50}$ values are calculated with a computer system using the formula $$IC_{50} = \frac{OD_{665}(\text{test}) - OD_{665}(\text{initial})}{OD_{665}(\text{control}) - OD_{665}(\text{initial})} \times 100$$

The $IC_{50}$ values are defined as that concentration of active ingredient at which the number of cells per depression at the end of the incubation time is only 50% of the number of cells in the control cultures. The $IC_{50}$ values of the compounds of the formula I are, for example, in the range from $10^{-6}$ to $2.5 \times 10^{-4}$ M.

The compounds of the formula I are thus particularly suitable for the treatment of disease states which respond to inhibition of ornithine decarboxylase, for example benign and malignant tumours. They can cause tumour regressions, and furthermore prevent the spread of tumour cells and the growth of micrometastases. They can moreover be used, for example, for the treatment of protozoa infections, for example trypanosomiasis, malaria or inflammation of the lung caused by Pneumocystis carinii.

Compounds of the formula I can display a good tolerability here. This can be demonstrated by experiments on rats: healthy male albino rats (Tif:RAIf (SPF), CIBA Animal Production, Stein, Switzerland) of initially 130 to 250 g are provided with a pelleted standard diet (NAFAG No. 890; NAFAG, Gossau, Switzerland) and water ad libitum. 20, 60 or 200 mg/kg of a compound of the formula I in 10 ml of aqueous solution (concentrations 0.2; 0.6; and 2.0%) are additionally administered daily to the rats for 14 days by separate artificial feeding. The following data, for example, are determined during the administration period: mortality, clinical symptoms, body weight, food consumption, water consumption, hearing, clinical biochemistry, haematology, urine analysis, necropsy. Result: the compounds of the formula I investigated are tolerated at doses of up to 200 mg/kg daily without obvious signs of toxicity.

The compounds of the formula I can be used as selective ODC inhibitors by themselves or also in combination with other pharmacologically active substances. Conceivable combinations are, for example, those with (a) inhibitors of other enzymes of polyamine biosynthesis, for example S-adenosylmethionine decarboxylase inhibitors, (b) inhibitors of protein kinase C, (c) inhibitors of tyrosine protein kinase, (d) cytokines, (e) negative growth regulators, (f) aromatase inhibitors, (g) antioestrogens or (h) conventional cytostatic active ingredients.

Preferred compounds of the formula I are those, in which the radical A is $C_3$–$C_6$cycloalkylene;

n is 0 or 1 and, independently thereof, m is 0 or 1;

with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, the compounds of the formula I existing in the cis or trans form or as mixtures of the cis or trans form, preferably in the cis or the trans form, in particular as pure enantiomers, if asymmetric carbon atoms are present; in particular in the trans form (as enantiomer mixtures or, in particular, as pure enantiomers, if asymmetric carbon atoms are present); and salts thereof.

Particularly preferred compounds of the formula I are those
in which the radical A is $C_3$–$C_6$cycloalkylene;

n is 0 and m is 0 or 1;

with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, the compounds of the formula I existing in the cis or trans form or as mixtures of the cis or trans form, preferably in the cis or the trans form, in particular as pure enantiomers, if asymmetric carbon atoms are present; in particular in the trans form (as enantiomer mixtures or, in particular, as pure enantiomers, if asymmetric carbon atoms are present); and salts thereof.

More particularly preferred compounds of the formula I are those
in which the radical A is $C_3$–$C_6$cycloalkylene;

n is 0 and m is 0;

with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, the compounds of the formula I existing in the cis or trans form or as mixtures of the cis or trans form, preferably in the cis or the trans form, in particular as pure enantiomers, if asymmetric carbon atoms are present; in particular in the trans form (as enantiomer mixtures or, in particular, as pure enantiomers, if asymmetric carbon atoms are present); and salts thereof.

Very particularly preferred compounds of the formula I are those
in which

A is 1,2-cyclopropylene; 1,3-cyclobutylene; 1,3-cyclopentylene; or 1,3- or 1,4-cyclohexylene;

m is 0 or 1 and n, independently of m, is 0 or 1;

with the proviso that the distance between the aminooxy radical $H_2N$—O— and the amino group —$NH_2$ is at least 3 and not more than 4 carbon atoms; the compounds of the formula I existing in the cis or trans form or as mixtures of the cis or trans form, preferably in the cis or the trans form, in particular as pure enantiomers, if asymmetric carbon atoms are present; in particular in the trans form (as enantiomer mixtures or in particular as pure enantiomers, if asymmetric carbon atoms are present); and salts thereof.

Especially preferred compounds of the formula I are those in which

A is 1,2-cyclopropylene; 1,3-cyclobutylene; 1,3-cyclopentylene; or 1,3- or 1,4-cyclohexylene;

m is 0 or 1 and n, independently of m, is 0 or 1;

with the provisos that a) the distance between the aminooxy radical H$_2$N—O— and the amino group —NH$_2$ is at least 3 and not more than 4 carbon atoms, b) n is 0 or 1, if A is 1,2-cyclopropylene or 1,3-cyclobutylene, and c) n is 0 if A is as defined, except for 1,2-cyclopropylene or 1,3-cyclobutylene; the compounds of the formula I existing in the cis or trans form or as mixtures of the cis or trans form, preferably in the cis or the trans form, in particular as pure enantiomers, if asymmetric carbon atoms are present; in particular in the trans form (as enantiomer mixtures or in particular as pure enantiomers, if asymmetric carbon atoms are present); and salts thereof.

Exceptionally preferred compounds of the formula I are those
in which

A is 1,2-cyclopropylene; 1,3-cyclobutylene; 1,3-cyclopentylene; or 1,3- or 1,4-cyclohexylene;

n is 0 and m is 0 or 1;

with the proviso that the distance between the aminooxy radical H$_2$N—O— and the amino group —NH$_2$ is at least 3 and not more than 4 carbon atoms; the compounds of the formula I existing in cis or trans form or as mixtures of the cis or trans form, preferably in the cis or the trans form, in particular as pure enantiomers, if asymmetric carbon atoms are present; in particular in the trans form (as enantiomer mixtures or in particular as pure enantiomers, if asymmetric carbon atoms are present); and salts thereof.

Highly preferred compounds of the formula I are those
in which

A is 1,4-cyclohexylene, n is 0 and m is 0, and which exist in the cis or trans form, in particular in the trans form, and salts thereof.

Highly preferred compounds of the formula I are also those
in which

A is 1,3-cyclobutylene, n is 0 and m is 0 or 1 (in particular m is 1), and which exist in the cis or trans form, in particular in the trans form, and salts thereof.

Highly preferred compounds of the formula I are also finally those
in which

A is 1,2-cyclopropylene, n is 0 or 1 and m is 1, and which exist in the cis or trans form, in particular in the cis form, and salts thereof.

The compounds of the formula I mentioned specifically in the examples and salts thereof, in particular pharmaceutically acceptable salts, are preferred above all others.

The novel compounds of the formula I and their salts can be prepared by processes known per se, for example by a procedure in which from a compound of the formula II

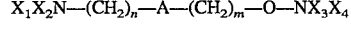  (II)

in which

A, n and m are as defined for compounds of the formula I, with the provisos that i) the distance between the radical —O—NX$_3$X$_4$ and the radical X$_1$X$_2$N— is at least 3 and not more than 4 carbon atoms and that ii) the two radicals X$_1$X$_2$N—(CH$_2$)$_n$— and —(CH$_2$)$_m$—O—NX$_3$X$_4$ are not bonded to the same ring carbon atom of A, and in which X$_1$, X$_2$, X$_3$ and X$_4$ independently of one another are hydrogen or a monovalent amino-protecting group, it also being possible for X$_1$ with X$_2$, X$_3$ with X4 or X$_1$ with X$_2$ and X$_3$ with X$_4$ in each case together to form a bivalent protecting group, and in which other functional groups which are not to participate in the reaction are present in protected form if necessary, with the proviso that at least one of the groups X$_1$, X$_2$, X$_3$ and X4 is an amino-protecting group, or a salt thereof, if salt-forming groups are present, the amino-protecting groups present are split off, and, if desired, a compound of the formula I which is obtainable is converted into another compound of the formula I, an isomer mixture which is obtainable is split into the isomers and/or a free compound of the formula I which is obtainable is converted into a salt or a salt of a compound of the formula I which is obtainable is converted into the free compound or into another salt.

DETAILED DESCRIPTION OF THE PREFERRED PROCESS VARIANTS

Unless stated otherwise, A, m and n in starting materials and end products below are as defined for compounds of the formula I. The provisos for compounds of the formula I are also to be applied accordingly.

Elimination of protecting groups:

The protecting groups for functional groups in starting materials, in particular for amino and hydroxyl groups, include, in particular, the conventional protecting groups which are usually used, for example, in the synthesis of peptide compounds, cephalosporins, penicillins, nucleic acid derivatives and sugars. These protecting groups can already be present in the intermediates and should protect the functional groups in question against undesirable side reactions. It is characteristic of protecting groups that they can easily be introduced and split off, i.e. without undesirable side reactions, and that they are not present in the end products.

Protecting groups and their removal are known per se and are described, for example, in J. F. W. McOmie, "Protective Groups in Organic Chemistry", Plenum Press, London, New York, 1973, and T. W. Greene, "Protective Groups in Organic Synthesis", Wiley, New York, 1984. Amino-protecting groups can be mono- or bivalent. Preferred monovalent amino-protecting groups X$_1$, X$_2$, X$_3$ and X$_4$ are acyl groups, preferably lower alkanoyl, such as formyl, acetyl or propionyl, halo-lower alkanoyl, such as 2-halogenoacetyl, in particular 2-chloro-, 2-bromo-, 2-iodo-, 2,2,2-trifluoro- or 2,2,2-trichloroace benzoyl which is unsubstituted or substituted, for example by halogen, lower alkoxy, lower alkoxycarbonyl or nitro, for example benzoyl, 4-chlorobenzoyl, 4-methoxybenzoyl, 2-methoxycarbonyl-benzoyl or 4-nitrobenzoyl, the acyl radical of a carbonic acid half-ester, in particular arylmethoxycarbonyl having one or two aryl radicals, which are preferably phenyl, naphthyl or 9-fluorenyl which is unsubstituted or mono- or polysubstituted, for example by lower alkyl, in particular tert-lower alkyl, such as tert-butyl, lower alkoxy, such as methoxy, hydroxyl, halogen, for example chlorine, and/or nitro, such as unsubstituted or substituted benzyloxycarbonyl, for example 4-nitrobenzyloxycarbonyl, or substituted diphenylmethoxycarbonyl, for example di-(4-methoxyphenyl)-methoxycarbonyl, 2-halo-lower alkoxycarbonyl, for example 2,2,2-trichloroethoxycarbonyl, 2-bromomethoxycarbonyl or 2-iodoethoxycarbonyl, lower alkoxycarbonyl, in particular a lower alkoxycarbonyl which is branched in the 1-position of the lower alkyl radical or suitably substituted in the 1- or 2-position, in particular tert-lower alkoxycarbonyl, for example tert-butoxycarbonyl, or primary lower alkoxycarbonyl, such as ethoxycarbonyl, alkylformimidoyl, such as lower alkyl-formimidoyl, for example tert-butylformimidoyl, sulfo ($-SO_3H$), which can also be present in salt form, such as in the form of an alkali metal or ammonium salt, for example as the sodium or potassium salt, or arylmethyl groups, such as mono-, di- or, in particular, triarylmethyl, the aryl radicals being, in particular, unsubstituted or substituted phenyl radicals, for example benzyl, diphenylmethyl or triphenylmethyl (trityl). Phenyl-lower alkyl-methyl, such as (R,S)—, (R)— or, in particular, 1(S)—phenylethyl, is also preferred. Tri-lower alkylsilyl, such as trimethylsilyl, is furthermore possible.

Particularly preferred monovalent amino-protecting groups $X_1$, $X_2$, $X_3$ and $X_4$ are acyl radicals of carbonic acid half-esters, in particular lower alkoxycarbonyl, for example tert-butoxycarbonyl or ethoxycarbonyl, benzyloxycarbonyl which is unsubstituted or substituted, for example as defined above, for example 4-nitro-benzyloxycarbonyl, diphenylmethoxycarbonyl or 2-halo-lower alkoxycarbonyl, such as 2,2,2-trichloroethoxycarbonyl; trityl; lower alkanoyl, such as formyl and acetyl, 2-methoxycarbonyl-benzoyl or lower alkylformimidoyl radicals, in particular those in which the lower alkyl radical is branched once or twice in the 1-position, such as tert-butyl-formimidoyl. The protecting group $X_1$ or $X_2$ preferred above all others is lower alkoxycarbonyl, for example tert-butoxycarbonyl, or lower alkanoyl, such as acetyl.

Preferred bivalent amino-protecting groups formed from the radicals $X_1$ and $X_2$ and/or $X_3$ and $X_4$ are mono- or disubstituted methylidene groups (resulting in oxime derivatives in the case of $X_3$ and $X_4$), such as 1-lower alkoxy(in particular methoxy or ethoxy)-lower alkylidene (for example -ethylidene or -1-n-butylidene), for example $=C(CH_3)(OC_2H_5)$, 1-lower alkyl(in particular methyl or ethyl)-lower alkylidene (in particular -1-ethylidene), for example $=C(CH_3)_2$, or 1-phenyl-lower alkylidene, for example $=CH$-phenyl, and hydrocarbyldicarboxylic acid radicals which are preferably bonded via both carbonyl groups to the nitrogen to be protected (resulting in bisacyl derivatives), in particular phthaloyl or hydrogenated analogues which are unsubstituted or substituted, for example by the same substituents as defined above for substituted benzoyl, for example the phthaloyl radical, which forms a 1H-isoindole-1,3-(2H)-dione radical (phthalimido group) together with the nitrogen atom to be protected, or corresponding dihydro-, tetrahydro- or hexahydro-phthaloyl radicals, lower alkyl-dicarboxylic acid radicals, such as the succinic acid radical, lower alkenyldicarboxylic acid radicals, such as the maleic acid radical, or $C_6$–$C_{12}$bicyclodicarboxylic acid radicals, such as the 5-norbornene-2,3-dicarboxylic acid radical.

The protecting groups are split off in the process according to the invention in a manner known per se, for example by means of solvolysis;, in particular hydrolysis, alcoholysis, acidolysis, aminolysis or hydrazinolysis, by means of reduction, in particular hydrogenolysis, by means of photolysis or with the aid of enzymatic methods; with simultaneous elimination of all the protecting groups present or stepwise elimination, it being possible for intermediates which are partly freed from protecting groups to be further used in non-purified or purified form. The elimination of the protecting groups is described, for example, in the above-mentioned standard works.

The amino-protecting group(s) is/are preferably split off in a manner known per se, stepwise or simultaneously, depending on the nature of the protecting group(s), for example by means of reduction or solvolysis, in particular hydrolysis, preferably in an acid medium, alcoholysis, acidolysis, aminolysis or hydrazinolysis. Lower alkoxycarbonyl, such as the tert-butyloxycarbonyl group, or the trityl radical can be liberated, for example, by treatment with an acid, such as a mineral acid, for example sulfuric acid or a hydrogen halide acid, such as hydrochloric acid, in the presence or absence of solvents, in particular water, alcohols, such as methanol or ethanol, or ethers, such as tetrahydrofuran or diethyl ether, or an organic acid, for example formic, acetic or trifluoroacetic acid, in the presence or absence of water or an organic solvent, for example methylene chloride, at preferred temperatures of $-20°$ C. up to the reflux temperature, in particular at $0°$ C. to room temperature or at the reflux temperature. Primary lower alkoxycarbonyl is preferably liberated under alkaline conditions, for example using hydroxy bases, such as alkali metal hydroxides, for example sodium hydroxide or potassium hydroxide, in water, aqueous solvents, such as alcohol/water mixtures, for example ethanol/water or methanol/water, or in alcohols, such as methanol or ethanol, at preferred temperatures as defined for acid splitting off of lower alkoxycarbonyl. The unsubstituted or substituted benzyloxycarbonyl group is split off, for example, reductively by hydrogenolysis, i.e. by treatment with hydrogen in the presence of a suitable catalyst, for example palladium, or by means of sodium in liquid ammonia, or by acidolysis, in particular by means of hydrogen bromide/glacial acetic acid. 2-Halo-lower alkoxycarbonyl can be split off, for example, by treatment with a suitable reducing agent, such as zinc, in the presence of an organic solvent, such as methanol or aqueous acetic acid. Lower alkyl-formimidoyl, such as tert-butylformimidoyl, is preferably split off by bases, such as hydroxides, in particular alkali metal hydroxides, for example potassium hydroxide. The hydrocarbyldicarboxylic acid radicals, in particular the phthaloyl group, can be split off, for example, by means of hydrazinolysis, for example with hydrazine hydrate in the presence or absence of further water (which can also first be added during the reaction) and/or organic solvents, such as alcohols, for example ethanol, or ethers, such as diethyl ether, at preferred temperatures of between $0°$ C. and the reflux temperature, for example at $20°$ to $30°$ C. or at the reflux temperature, by means of aminolysis, for example with primary amines, such as lower alkylamines, for example butylamine, cycloalkylamines, for example cyclohexylamine, or arylamines, such as aniline, or by means of ammonium salts, preferably in polar solvents, such as alcohols, for example methanol or ethanol, in the presence or absence of liquid chlorinated hydrocarbons, such as methylene chloride or chloroform, or (if ammonium hydroxide is used as the base) in water, at preferred temperatures of $50°$ C. to the reflux temperature, in particular at the reflux temperature, or by means of an acid, in particular a mineral acid, for example sulfuric acid or a hydrogen halide acid, such as hydrochloric acid, in water in the presence or absence of organic solvents, for example alcohols, such as methanol, at preferred temperatures of between 50° C. and the reflux temperature, in particular at the reflux temperature. Unsubstituted or substituted benzoyl is preferably split off under alkaline or acid conditions, for example with hydroxide bases, such as alkali metal hydroxides, for example sodium hydroxide or potassium hydroxide, in water or aqueous solvents, such as water/alcohol mixtures, for example water/ethanol or water/methanol, at preferred temperatures of between 50° C. and the boiling temperature of the reaction mixture, in particular at the reflux temperature, or in the presence of sulfuric acid or hydrogen halide acids, such as hydrochloric acid, in water or aqueous solvents, such as water/alcohol mixtures, for example water/methanol or water/ethanol, at preferred temperatures, as described for the liberation in the presence of hydroxide bases. For liberation of lower alkanoyl protecting groups, alkaline hydrolysis is preferably used, for example by means of hydroxy bases, such as alkali metal hydroxides, for example sodium hydroxide or potassium hydroxide, in water or aqueous solutions at preferred temperatures of 50° C. up to the reflux temperature, for example at the reflux temperature, or acid hydrolysis, for example with a mineral acid, such as a hydrogen halide acid or sulfuric acid, for example aqueous hydrochloric acid or sulfuric acid, under the influence of heat, for example at the temperatures mentioned last. Sulfo (including in salt form) is preferably removed by being split off under acid conditions, in particular with sulfuric acid or hydrogen halide acids, such as hydrochloric acid, in water or aqueous solvents, at preferred temperatures of between 50° C. and the reflux temperature, for example in the context of steam distillation. 1-Lower alkyl-lower alkylidene is preferably split off under acid conditions, for example in the presence of sulfuric acid or a hydrogen halide acid, such as hydrochloric acid, in water or an aqueous solvent at preferred temperatures of between 50° C. and the boiling temperature of the reaction mixture, for example under reflux or steam distillation. 1-Lower alkoxy-lower alkylidene is preferably liberated by reaction in the presence of acids, such as sulfuric acid or hydrogen halide acids, for example hydrochloric acid, in organic solvents, such as ethers, for example diethyl ether, in the presence of water at preferred temperatures of between 0° and 50° C., in particular at room temperature. Phenyl-lower alkyl-methyl, such as 1(S)-phenylethyl, can be split off by hydrogenation, for example with hydrogen in the presence of a noble metal catalyst, such as palladium, which can be bonded to a support material, such as aluminium oxide, silica gel, barium sulfate, strontium sulfate, calcium carbonate or charcoal, in an alcohol, such as a lower alkane hydroxide, for example ethanol, at temperatures of from 0° C. up to the reflux temperature, for example at about 50° C., preferably under normal pressure.

The starting materials of the formula II can be prepared by processes known per se, for example by methods analogous to those described in Houben-Weyl, Methoden der Organischen Chemie (Methods of Organic Chemistry), Volume X/1 (1971) and Volume E 16a (1990).

The compounds of the formula II are preferably prepared from starting materials of the formula III $X_1X_2N$—$(CH_2)_n$—A—$(CH_2)_m$—$W_1$  (III)

in which

A, n and m are as defined for compounds of the formula I, with the provisos that a) the distance between the radical —$W_1$ and the radical $X_1X_2N$— is at least 3 and not more than 4 carbon atoms and that b) the two radicals —$(CH_2)_m$—$W_1$ and $X_1X_2N$—$(CH_2)_n$— are not bonded to the same ring carbon atom of A: and in which $X_1$ and $X_2$ independently of one another are hydrogen or a monovalent amino-protecting group, with the proviso that at least one of the radicals $X_l$ and $X_2$ is an amino-protecting group, or $X_1$ and $X_2$ also together can form a bivalent protecting group, and $W_1$ is hydroxyl or a leaving group, or salts thereof; by reaction with a hydroxylamine of the formula IV $X_3X_4N$—OH  (IV)

in which $X_3$ and $X_4$ are as defined for compounds of the formula II, or an acid addition salt thereof.

In a compound of the formula III, a radical $W_1$ is hydroxyl or a leaving group, preferably a derivatized hydroxyl group, for example sulfonyl substituted by aliphatic or aromatic substituents, such as lower alkanesulfonyloxy, for example methanesulfonyloxy, or arylsulfonyloxy (=aryl-$SO_2$—O—), in which aryl has 6 to 14 carbon atoms, preferably as phenyl, naphthyl, indenyl or indanyl, and is unsubstituted or substituted by up to three radicals, for example by lower alkyl, such as methyl, lower alkoxy, such as methoxy, or halogen, such as fluorine, chlorine or bromine, for example lower alkylphenylsulfonyloxy (=lower alkylphenyl-$SO_2$—O—), such as p-toluenesulfonyloxy, a substituted lower alkanesulfonyl group, such as halo-lower alkanesulfonyl, for example trifluoromethanesulfonyl, or, in particular, a free hydroxyl group or a halogen atom, for example chlorine, bromine or iodine.

If $W_1$ is hydroxyl, which is the case in a preferred embodiment of the preparation process of the compound of the formula II, the reaction is preferably carried out by an intramolecular dehydration reaction. A particularly suitable reaction is a variant of the Mitsunobu reaction (in analogy to Synthesis, 682 (1976)), in which the compound of the formula III is reacted with an amino-protecting hydroxylamine of the formula IV, as defined above, in which the amino function is preferably protected by one of the above-mentioned bivalent amino-protecting groups, for example N-hydroxyphthalimide, N-hydroxy-5-norbomene-2,3-dicarboxylic acid imide or acetohydroxamic acid ethyl ester, in particular N-hydroxyphthalimide, and triarylphosphine, in which aryl preferably has 6 to 14 carbon atoms and is mono-, bi- or tricyclic, such as phenyl, naphthyl, indenyl or indanyl, for example triphenylphosphine, and an N,N'-azodicarboxylic acid diester, such as an N,N'-azodicarboxylic acid di-lower alkyl ester, for example diethyl N,N'-azodicarboxylate, preferably in an aprotic solvent, such as an ether, for example a cyclic ether, such as tetrahydrofuran, or, in particular, an aromatic solvent, such as benzene, toluene or xylene, without an inert gas or under an inert gas, such as nitrogen or argon, and at preferred temperatures of from 0° C. to 80° C., in particular from 10° to 40° C., for example at 20° to 30° C. The reaction is preferably carried out such that inversion takes place on the carbon atom carrying the hydroxyl group.

The reaction results in an aminooxy group protected by a bivalent amino-protecting group, in particular a hydrocarbyldicarboxylic acid radical bonded via both carbonyl groups, in a compound of the formula II which is obtainable.

Hydroxyl $W_1$ can also be converted into lower alkoxycarbonylaminoxy by nitrene insertion by reaction of N-carbonic acid lower alkyl ester-azides, such as carbonic acid ethyl ester-azide ($H_5C_2$—O—(C=O)—$N_3$), in organic solvents, for example carboxylic acid amides, such as dimethylformamide, or ethers, such as di-lower alkyl ethers, for example diethyl ether, at temperatures between 20° C. and the reflux temperature, preferably at the reflux temperature.

If $W_1$ is derivatized hydroxyl as described above, in particular a halogen atom, for example a bromine atom, or arylsulfonyl, such as toluenesulfonyl, the reaction is preferably carried out with an amino-protected hydroxylamine of the formula IV
in which $X_3$ and $X_4$ together are the hydrocarbyldicarboxylic acid radical bonded via both carbonyl groups or a mono- or disubstituted methylidene group, as defined above, in particular 1-lower alkyl-alkylidene or 1-lower alkoxy-lower alkylidene; and in which $X_3$ is sulfo and $X_4$ is sulfo; or in which one of the radicals $X_3$ and $X_4$ is hydrogen and the other is an acyl group, as defined above, in particular lower alkoxycarbonyl, benzyloxycarbonyl, 2-halo-lower alkoxycarbonyl, lower alkyl-formimidoyl, unsubstituted or substituted benzoyl, lower alkanoyl or sulfo. The reaction of the compound of the formula III with the compound of the formula IV in this case is preferably carried out in an organic solvent, such as an aromatic solvent, for example benzene, toluene or xylene, in alcohols, such as lower alkanols, for example methanol or ethanol, in polar solvents, such as di-lower alkyl-carboxylic acid amides, for example dimethylformamide, di-lower alkylsulfoxides, such as dimethylsulfoxide, nitriles, such as acetonitrile, ketones, such as di-lower alkyl ketones, for example acetone, or ethers, such as cyclic ethers, for example tetrahydrofuran or dioxane, water (if necessary in the presence of detergents, for example Zephirol® (=benzyl-dodecyl-dimethylammonium chloride and homologues, which contain other alkyl radicals instead of dodecyl; Bayer, Federal Republic of Germany), or mixtures of the solvents mentioned, anhydrous conditions or the absence of protic solvents being preferred if the reaction is impaired too greatly by water or protic solvents (for example because of hydrolysis or solvolysis of the reagents); in the absence or presence of basic reagents or of catalysts, in particular of bases, for example carbonate or bicarbonate salts, such as alkali metal carbonates, for example potassium carbonate or bicarbonate or sodium carbonate or bicarbonate (if necessary in the presence of crown ethers, such as dibenzo-18-crown-6), alkali metal hydrides, such as sodium hydride, alkali metal amides, such as sodium amide, alkali metal alcoholates, such as sodium methoxide or sodium ethoxide (which can also be prepared in situ by addition of an alkali metal to the alcohol in question), sterically hindered amines, such as tertiary amines, for example triethylamine, N,N,N',N'-tetramethyl-methylenediamine or 1,8-diazabicyclo[5.4.0]undec-7-ene(1,5-5), hydroxides, such as alkali metal hydroxides, for example sodium hydroxide or potassium hydroxide, or without bases, by employing the salts of the compounds of the formula IV directly or preparing them in situ (for example by addition of an alkali metal, such as sodium or potassium); at preferred temperatures of between 0° C. and the reflux temperature or with evaporation, in particular at 20° C., 40° to 80° C., at the reflux temperature or with evaporation; with or without an inert gas, such as argon or nitrogen, it being possible for the expert to select the particular suitable conditions.

The preferred process for the preparation of the compounds of the formula I is the reaction of compounds of the formula III and IV to give compounds of the formula II with subsequent elimination of protecting groups as defined in the process in successive reaction steps.

The compounds of the formulae III and IV are known, are commercially obtainable or can be prepared by processes known per se.

The compounds of the formula III can be prepared, for example, by processes analogous to those described in Houben-Weyl, Methoden der Organischen Chemie (Methods of Organic Chemistry), Volume X/1 (1971) and Volume E 16a (1990)).

In particular, they are prepared as follows:

Preferably, compounds of the formula V

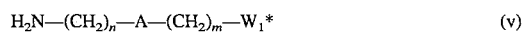

$$H_2N—(CH_2)_n—A—(CH_2)_m—W_1^* \qquad (v)$$

in which $W_1^*$ is hydroxyl,

A, n and m are as defined for compounds of the formula I, with the provisos that a) the distance between the radical —$W_1^*$ and the radical $H_2N$— is at least 3 and not more than 4 carbon atoms and that b) the two radicals —$(CH_2)_m$—$W_1^*$ and $H_2N$—$(CH_2)_n$— are not bonded to the same ring carbon atom of A (these compounds correspond to compounds in which, in the formula III, $W_1$ is hydroxyl, $X_1$ and $X_2$ are replaced by hydrogen atoms and the remaining radicals are as defined for compounds of the formula III), are convened into compounds of the formula III in which $W_1$ is hydroxyl by reaction with reagents which introduce amino-protecting groups $X_1$ and/or $X_2$ under conditions such as are described in the abovementioned standard works or below for introduction of protecting groups in the preparation of compounds of the formula IV (instead of $X_3$ or $X_3'$ and $X_4$ or $X_4'$, $X_1$ and $X_2$ being used in the starting compounds here).

For example, acyl groups $X_1$ or $X_2$ are introduced by customary methods for acylation of amino groups and for introduction of protecting groups.

A particularly preferred preparation is that of those compounds of the formula III
in which one of the radicals $X_1$ and $X_2$ is hydrogen and the other is a radical of an acyl radical of a carbonic acid half-ester, in particular lower alkoxycarbonyl, such as tert-butoxycarbonyl, or benzyloxycarbonyl, and the remaining radicals are as defined, from compounds of the formula V by reaction of an activated acid derivative of the formula VI

$$Q—W_2 \qquad (VI)$$

in which

Q is the acyl radical of a carbonic acid half-ester, in particular lower alkoxycarbonyl or benzyloxycarbonyl, while $W_2$ is a reactively derivatized hydroxyl group, preferably azolido, such as imidazolido, halogen, such as chlorine or bromine, or, in particular, an acyl radical, bonded via oxa, of a carbonic acid half-ester which is identical to Q (the compound of the formula VI is then a symmetric acid anhydride, i.e. a diester of dicarbonate). The activated acid derivative of the formula VI can also be prepared in situ, for example by reaction in the presence of carbodiimides, for example N,N'-di-lower alkyl- or N,N'-di-$C_5$-$C_7$cycloalkylcarbodiimide, such as diisopropylcarbodiimide or N,N'-dicyclohexylcarbodiimide, advantageously in the presence of an activation catalyst, such as N-hydroxysuccinimide or N-hydroxybenzotriazole which is unsubstituted or substituted by halogen, lower alkyl or lower alkoxy. If expedient and appropriate, a salt, for example an alkali metal halide, such as sodium chloride, can be added.

The reaction is preferably carried out in an inert solvent, such as an ether, for example an aliphatic ether, such as diethyl ether, or a cyclic ether, such as tetrahydrofuran or dioxane, or an N,N-di-lower alkyl-lower alkanecarboxylic acid amide, such as dimethylformamide, or mixtures thereof; it also being possible for water to be present, in particular if cyclic ethers or N,N-di-lower alkyl-lower alkanecarboxylic acid amides are used; at temperatures of between 0° C. and the reflux temperature, preferably between 15° and 35° C., for example at room temperature. Bases, for example tertiary amines, such as triethylamine, diisopropylethylamine, 4-dimethylaminopyridine, N-methylmorpholine or pyridine, are added if necessary.

It may be desirable to protect the hydroxyl group $W_1$ present in formula V before introduction of one of the protecting groups $X_1$ and $X_2$ or a bivalent protecting group formed from the two.

A hydroxyl group can be protected, for example by a monovalent protecting group, such as an acyl group, for example lower alkanoyl which is unsubstituted or substituted by halogen, such as chlorine, such as acetyl or 2,2-dichloroacetyl, or, in particular, by an acyl radical of a carbonic acid half-ester as defined for protected amino groups. A preferred hydroxyl-protecting group is, for example, 2,2,2-trichloroethoxycarbonyl, 4-nitrobenzyloxycarbonyl or diphenylmethoxycarbonyl. A hydroxyl group can also be protected by tri-lower alkylsilyl, for example trimethylsilyl, triisopropylsilyl, tert-butyl-dimethylsilyl or, in particular, dimethyl-(2,3-dimethyl-2-butyl)silyl (=thexyldimethylsilyl), an etherifying group which can easily be split off, for example an alkyl group, such as left-lower alkyl, for example tert-butyl, an oxa- or a thia-aliphatic or -cycloaliphatic, in particular 2-oxa- or 2-thia-aliphatic or -cycloaliphatic, hydrocarbon radical, for example 1-lower alkoxyolower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thiacycloalkyl having 5-7 ring atoms, such as 2-tetrahydrofuryl or 2-tetrahydropyranyl, or a corresponding thia analogue, and by 1-phenyl-lower alkyl, such as benzyl, diphenylmethyl or trityl, in which the phenyl radicals can be unsubstituted or substituted, for example by halogen, for example chlorine, lower alkoxy, for example methoxy, and/or nitro. A protected hydroxyl group is preferably protected by lower alkoxycarbonyl or tri-lower alkylsilyl, in particular by trimethylsilyl, tert-butyl-dimethylsilyl, dimethyl-(2,3-dimethyl-2-butyl)silyl or tert-butoxycarbonyl.

If necessary, hydroxyl-protecting groups are introduced into the starting materials of the formula V by methods known per se. Examples of suitable reaction conditions are described, for example, in the abovementioned standard works of J. F. W. McOmie and T. W. Greene.

For example, a tri-lower alkylsilyl protecting group is converted into a hydroxyl group protected by tri-lower alkylsilyl by reaction of the: hydroxyl group in a compound of the formula V with a tri-lower alkylsilyl halide, such as tri-lower alkylsilyl chloride, in an inert solvent, such as a lower alkyl cyanide, for example acetonitrile, in the presence of a tertiary nitrogen base, such as 1,8-diazabicyclo [5.4.0]undec-7-ene, at temperatures between 0° and 50° C., in particular between 15° and 30° C.

After introduction of the amino-protecting groups $X_1$ and $X_2$, the hydroxyl-protecting group can be split off from the corresponding amino-protected compound of the formula III without simultaneous elimination of the amino-protecting group.

A hydroxyl group protected by a suitable acyl group or by unsubstituted or substituted 1-phenyl-lower alkyl is liberated analogously to a correspondingly protected amino group. A hydroxyl group protected by 2,2-dichloroacetyl is liberated, for example, by basic hydrolysis, and a hydroxyl group protected by tert-lower alkyl or by a 2-oxa- or 2-thia-aliphatic or -cycloaliphatic hydrocarbon radical is liberated by acidolysis, for example by treatment with a mineral acid or a strong carboxylic acid, for example trifluoroacetic acid.

Tri-lower alkylsilyl, such as trimethylsilyl or dimethyl-(2,3-dimethyl-2-butyl)silyl, is preferably split off by solvolysis, for example with alcohols, such as methanol or ethanol, at temperatures between 20° C. and the reflux temperature. A tri-lower alkylsilyl group is also split off by acidolysis with a mineral acid, in particular hydrofluoric acid, or a strong carboxylic acid, such as trifluoroacetic acid, or by reaction with the fluoride salt of a metal or a base which liberates fluoride ions, for example the acid addition salt of hydrogen fluoride and a nitrogen base or a metal fluoride, such as an alkali metal fluoride, for example sodium fluoride or potassium fluoride, in the presence of absence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride, tetrabutylammonium fluoride or N-benzyl-trimethylammonium fluoride, in the presence of aprotic, polar solvents, such as ethers, for example tetrahydrofuran or dioxane, dimethylsulfoxide or N,N-dimethylacetamide, at preferred temperatures of about –20° to 50° C., for example between 0° C. and room temperature.

2-Halo-lower alkoxycarbonyl as the hydroxyl-protecting group is removed by reducing agents, for example reducing metal, such as zinc, reducing metal salts, such as chromium (II) salts, or by sulfur compounds, for example sodium dithionite or, preferably, sodium sulfide and carbon disulfide.

The introduction and elimination of tri-lower alkylsilyl as the hydroxyl-protecting group, as defined above, is particularly preferred, especially if the radical of a carbonic acid half-ester, in particular lower alkoxycarbonyl, is present as the amino-protecting group $X_2$ or $X_2$.

Compounds of the formula III in which $W_1$ is a leaving group can be prepared, for example, from compounds of the formula III in which $W_1$ is hydroxyl by reaction with the corresponding nucleophiles, for example a sulfonyl halide, such as sulfonyl bromide or sulfonyl chloride, substituted by aliphatic or aromatic substituents, such as a lower alkanesulfonyl halide, for example methanesulfonyl chloride, or arylsulfonyl halide (for example aryl-$SO_2$—Cl; —Br), in which aryl has 6 to 14 carbon atoms, for example as phenyl, naphthyl, indenyl or indanyl, and is unsubstituted or substituted by up to three radicals, for example by lower alkyl, such as methyl, lower alkoxy, such as methoxy, or halogen, such as fluorine, chlorine or bromine, for example lower alkylphenylsulfonyl chloride (=lower alkylphenyl-SO$_2$—Cl), such as p-toluenesulfonyl chloride, a substituted lower alkanesulfonyl halide, such as halo-lower alkanesulfonyl chloride, for example trifluoromethanesulfonyl chloride, or a hydrogen halide acid, in particular hydrochloric, hydrobromic or hydriodic acid, if necessary in a suitable solvent, for example a halogenated hydrocarbon, such as chloroform, methylene chloride or dichloroethane, in the absence (in particular if the hydrogen halide acids are used) or presence of a tertiary nitrogen base, such as a tri-lower alkylamine, for example methylamine or ethyldiisopropylamine, pyridine or dimethylaminopyridine, at temperatures of between −78° C. and the reflux temperature, in particular from −5° to 30° C. The conditions mentioned are preferably suitable for introduction of the leaving groups $W_1$ apart from halogen. Halogen radicals can preferably be introduced by reaction of the corresponding compounds in which $W_1$ is sulfonyloxy substituted by aliphatic or aromatic substituents, with, for example, a halide, in particular a metal halide, for example a metal chloride, bromide or iodide, such as an alkali metal chloride, bromide or iodide or alkaline earth metal chloride, bromide or iodide, in suitable solvents, for example di-lower alkylketones, such as acetone, at preferred temperatures of from −20° C. up to the reflux temperature, for example at 10° to 30° C., if appropriate in the presence of copper, for example in small pieces or as a powder, in the case of iodides.

It is also possible to prepare compounds of the formula III protected by amino-protecting groups $X_1$ and/or $X_2$ directly without having to proceed via intermediates of the formula V having a free amino group.

Thus, compounds of the formula III
in which
  m is 1 and
in which
  one of the radicals $X_1$ and $X_2$ is hydrogen and the other is hydrogen or a monovalent amino-protecting group as defined for compounds of the formula II and
  n is 0 or 1,
with the provisos as defined for compounds of the formula III, can also be prepared by a procedure in which a compound of the formula VII

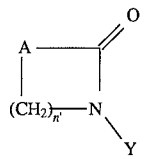
(VII)

in which
  Y is a monovalent amino-protecting group as defined above for $X_1$ or $X_2$, in particular lower alkoxycarbonyl,
  A is as defined for compounds of the formula I and
  n' is 0 or 1,
with the proviso that a) the ring formed with the aid of A and —(C=O)—(N—Y)—[(CH$_2$)$_{n'}$]— has 4 or 5 ring members and the two bonds of the radical —(C=O)—(N—Y)—[(CH$_2$)$_{n'}$]— do not originate from the same carbon atom of A, is reacted with reduction of the amide bond. The reduction, which takes place with simultaneous ring opening, is preferably carried out with suitable complex hydrides, such as lithium aluminium hydride in ethers, such as diethyl ether, sodium borohydride in alcohols (preferably), such as methanol or ethanol, or disiamylborane (bis(3-methyl-but-1-yl)borane) in ethers, such as tetrahydrofuran, at temperatures of between −20° and 50° C., in particular between −5° and 25° C. Since Y is as defined for $X_1$ or $X_2$ as defined above for compounds of the formula II, in particular lower alkoxycarbonyl, corresponding compounds of the formula III in which $W_1$ is hydroxyl can be obtained here directly.

The bonds of the radical A are preferably in the cis configuration; a corresponding cis compound of the formula III is then obtained.

Compounds of the formula VII are known or can be prepared by processes known per se.

For example, a cis compound of the formula VII
in which
  Y is the acyl radical of a carbonic acid half-ester as the amino-protecting group,
  A is 1,3-cyclopentylene and
  n' is 0,
can be prepared by reaction of the corresponding intermediate with the name 2-azabicyclo[2.2.1]heptan-3-one, in which Y is replaced by a hydrogen atom, by acylation with a compound of the formula VI as defined below in the presence of 4-dimethylaminopyridine under conditions analogous to those defined above for the reaction of the compound of the formula VI, preferably (Y=tert-lower alkoxycarbonyl, such as tert-butoxycarbonyl) with a di-tert-lower alkyl dicarbonate, such as di-tert-butyl dicarbonate, in the presence of a catalytic amount of 4-dimethylaminopyridine in an organic solvent, for example an ether, such as tetrahydrofuran. 2-Azabicyclo[2.2.1]heptan-3-one is obtained, for example, by reduction of the double bond of 2-azabicyclo[2.2.1]hept-5-en-3-one, in particular by hydrogenation in the presence of a catalyst, such as palladium, platinum or ruthenium, in particular bonded to a support, such as charcoal, if necessary under increased pressure, for example under 1 to 10 bar, in a suitable hydrogenation apparatus, for example a Parr apparatus, at temperatures of from 0° to 50° C., in particular from 15° to 30° C., in a solvent, such as an ester, for example ethyl acetate. 2-Azabicyclo[2.2.1]hept-5-en-3-one is obtained, for example, by reaction of 3-tosyl-2-azabicyclo[2.2.1]hepta-2,5-diene in a lower alkanoic acid, such as acetic acid, at temperatures of between 0° and 40° C., in particular between 15° and 30° C.; 3-tosyl-2-azabicyclo[2.2.1]hepta-2,5-diene is obtained, for example, by cycloaddition of tosyl cyanide onto cyclopentadiene (the latter acts as the solvent) at temperatures of between 0° and 50° C., in particular at 15° to 30° C.

Further compounds of the formula VII can be prepared analogously by thermal or photochemical cycloaddition of tosyl cyanide onto double bonds and analogous continuation of the synthesis as described for 3-tosyl-2-azabicyclo[2.2.1]hepta-2,5-diene.

From compounds of the formula VIII

HO—(CH$_2$)$_m$—A*—(CH$_2$)$_n$—NH—Y' (VIII)

in which
  A* is a 3- to 6-membered cyclic hydrocarbon radical having one or more unsaturated bonds (excluding cyclobutadienylene),
  Y' is a monovalent amino-protecting group as defined above for $X_1$ or $X_2$, in particular lower alkanoyl, such as acetyl, or hydrogen,
  and the other definitions and provisos are analogous to those for compounds of the formula I,
with the provisos that a) the distance between the radical —OH and the radical Y'—HN— is at least 3 and not more than 4 carbon atoms and that b) the two radicals —(CH$_2$)$_m$—OH and Y'—HN—(CH$_2$)$_n$— are not bonded to the same ring carbon atom of A*, corresponding compounds of the formula III (Y'=amino-protecting group) or V (Y'=hydrogen) can also be prepared by reduction of the unsaturated bonds in the ring A*. Unsaturated bonds are preferably double bonds and A* is preferably chosen from phenylene, cyclopentenylene, cyclopentadienylene, cyclobutenylene and cyclopropenylene, in particular phenylene.

The reduction is preferably carried out by hydrogenation in the presence of a suitable catalyst, in particular a base heavy metal or oxides thereof, such as nickel or cobalt (preferably nickel or Raney nickel in alcohols, such as ethanol, or in particular in aqueous alkalies, such as alkali metal hydroxide solution, for example aqueous sodium hydroxide solution, at temperatures of from 150° to 190° C. under increased pressure, for example under 50 to 200 bar), or noble metals or noble metal oxides, such as platinum, platinum oxide, palladium, palladium oxide or ruthenium (preferably in suitable solvents chosen from alcohols, such as methanol or ethanol, esters, such as ethyl acetate, ethers, such as dioxane, and water, or in suitable mixtures of the solvents mentioned; in the presence or absence of lower alkanoic acids, such as acetic acid, or under basic conditions, it also being possible for the catalysts mentioned to be bonded to support materials, such as charcoal, barium sulfate, strontium sulfate, calcium carbonate, aluminium oxide or silica gel; at suitable temperatures, in particular between 0° and 50° C., for example at room temperature; if necessary under increased pressure, for example under between about 1 and 20 bar).

Analogously to the hydrogenation of the compounds of the formula VIII, the hydrogenation of analogous compounds in which —NH—Y' is replaced by a nitro group is also possible; the hydrogenation then preferably takes place with Raney nickel under pressures of 50 to 80 bar and at temperatures of from 150° to 190° C. in aqueous alkalies, such as sodium hydroxide solution. Corresponding compounds of the formula V are obtained directly.

Compounds of the formula VIII are known or can be prepared by processes known per se, as is also the case with analogues thereof in which —NH—Y' is replaced by a nitro group.

The compounds of the formula IV can be prepared, for example, as follows:

If X$_3$ or X$_4$ is a monovalent amino-protecting group, for example an acyl radical, as defined above, free hydroxylamine or a salt thereof can be converted into the N-protected form by reaction with the acid of the formula IX or X which results in the acyl radical

   (IX)

   (X)

in which

X$_3$' and X$_4$' are acyl, as defined above as the amino-protecting group, or with an activated derivative thereof, which can also first be formed in situ, by customary methods for acylation of amino groups and for introduction of protecting groups, as described, for example, in the standard works mentioned above and below. If X$_3$' or X$_4$' is, for example, lower alkanoyl or unsubstituted or substituted benzoyl, the activated derivative, in which the hydroxyl group in formula IX or X is replaced by an activated hydroxyl group, may be, for example, acyloxy, in which acyl is a radical which is other than or preferably the same as X$_3$' or X$_4$', azido, azolido, such as imidazolido, halo, such as chloro or bromo, or nitrophenoxy; for example the corresponding acid anhydride, acid azide or acid halide, in particular the corresponding acid chloride. The preparation of an activated acid derivative in situ is carried out, for example, by reaction in the presence of carbodiimides, for example N,N'-di-lower alkyl- or N,N'-di-C$_5$-C$_7$cycloalkyl-carbodiimide, such as diisopropylcarbodiimide or N,N'-dicyclohexylcarbodiimide, advantageously in the presence of an activation catalyst, such as N-hydroxysuccinimide, or N-hydroxybenzotriazole which is unsubstituted or substituted by halogen, lower alkyl or lower alkoxy. Bases, for example tertiary amines, such as triethylamine, diisopropylethylamine, dimethylaminopyridine, N-methylmorpholine or pyridine, are added if necessary. If X$_3$' or X$_4$' is the radical of a half-ester of carbonic acid, the hydroxyl group in X$_3$' or X$_4$' is preferably present in a compound of the formula IX or X as an activated hydroxyl group as defined above; in particular, the hydroxyl group is then replaced by halogen, such as chlorine or bromine, or an azolyl radical, such as imidazolyl.

Alkylformimidoyl radicals X$_3$ or X$_4$ are introduced into hydroxylamine, for example, by a method analogous to that described by Meyers, A. et at., in J. Am. Chem. Soc. 106, 3270 (1984); the tert-butylformimidoyl radical is introduced, for example, by reaction of the free hydroxylamine with N,N-dimethyl-N'-tert-butylformamidine in the presence of a catalytic amount of ammonium sulfate in toluene at the reflux temperature, or alternatively by reaction of tert-butylformamide with Et$_3$O$^+$BF$_4^-$ in methylene chloride at room temperature, addition of the amino compound and further reaction in the temperature range from room temperature to 40° C.

Hydroxylaminedisulfonic acid (X$_3$ and X$_4$=sulfo in compounds of the formula IV), and in particular its alkaline earth metal or ammonium salts, are prepared, for example, by reaction of a concentrated solution of an alkali metal nitrite with alkali metal hydrogen sulfate, or corresponding ammonium salts, and sulfur dioxide.

Arylmethyl X$_3$ and/or X$_4$ in compounds of the formula IV can be introduced, for example, by reaction of hydroxylamine with arylmethyl halides, in particular arylmethyl chlorides or bromides, with nucleophilic replacement of the halogen atom, preferably by reaction in the presence of a tertiary amine, such as methylamine or pyridine, in an aprotic solvent, such as an ether, for example tetrahydrofuran or dioxane, or a carboxylic acid amide, such as di-lower alkylformamide, for example dimethylformamide.

If X$_3$ and X$_4$ in compounds of the formula IV together are a bivalent amino-protecting group, the following preparation processes are preferred for preparation of these starting compounds:

Oxime derivatives of the formula IVa

   (IVa)

in which

X$_{iii}$ is a bivalent mono- or disubstituted methylidene group as defined above for compounds of the formula II in the case of X$_3$ and X$_4$, can be prepared from corresponding aldehyde or ketone intermediates in which =N—OH in formula IVa is replaced by a double-bonded oxygen (=O) under conditions customary for reaction of aldehydes or ketones with amino compounds, hydroxylamine, preferably as a salt, in particular with an inorganic acid, such as a hydrogen halide acid, for example hydrochloric acid, with sulfuric acid, for example as a sulfate or hydrogen sulfate, with phosphoric acid, for example as a phosphate, hydrogen phosphate or dihydrogen phosphate, with an organic acid, such as a lower alkanoic acid which is substituted in the lower alkyl radical by halogen, such as fluorine, chlorine or iodine, or is preferably unsubstituted, such as acetic acid, chloroactic acid, dichloroacetic acid or trifluoro- or trichloroacetic acid, a sulfonic acid, such as a lower alkanesulfonic acid, for example methane- or ethanesulfonic acid or ethanedisulfonic acid, or with an aromatic sulfonic acid, such as benzene-or naphthalenesulfonic acid or naphthalene-1,5-disulfonic acid, or in the form of a double salt, such as $Zn(NH_2OH)_2Cl_2$ (Crismers reagent); being reacted with the corresponding aldehyde or ketone in water, an aqueous solvent mixture, such as mixtures of water with alcohols, for example methanol or ethanol, di-lower-alkyl sulfoxides, such as dimethyl sulfoxide, or di-lower alkyl-lower alkanoylamides, such as dimethylformamide, or in organic solvents, such as those mentioned last, or sufficiently inert nitriles, such as acetonitrile, mixtures thereof or liquid ammonia, preferably in aqueous-alcoholic solution, for example in methanol/water or ethanol/water; at temperatures of between −78° C. and the reflux temperature, preferably from −30° to 100° C., in particular from 5° to 90° C., for example at about 80° C.; under pressures of 1 to 10,000 bar, preferably under normal pressure if hydroxylamine salts are used; in the absence of a base or preferably, in the case of acid salts of the hydroxylamine, buffering of the acid with a base, in particular a hydroxy base, such as an alkali metal hydroxide, for example sodium hydroxide or potassium hydroxide, with a carbonate or bicarbonate, in particular an alkali metal carbonate or bicarbonate or alkaline earth metal carbonate or bicarbonate, for example sodium carbonate or potassium carbonate or sodium bicarbonate or potassium bicarbonate, with a salt of a weak organic acid, in particular an alkali metal salt of a lower alkanecarboxylic acid, for example sodium acetate or potassium acetate, with organic nitrogen bases, in particular sterically hindered (secondary or tertiary) amines, such as pyrrolidine, or pyridine, or with an anion exchanger, for example Amberlite® IR-4B, the presence of an alkali metal carbonate being particularly preferred. The compounds of the formula IVa in which $X_{iii}$ is 1-lower alkoxy-lower alkylidene, on the other hand, are obtainable, for example, analogously to the process accessible via Chem. Abstr. 73, 25359 and 66520 (1970).

Hydrocarbyldicarboxylic acid derivatives of the formula IVa,
in which $X_{iii}$ is a hydrocarbyldicarboxylic acid radical bonded via both carbonyl groups as defined above for $X_3$ and $X_4$ in compounds of the formula II, can be prepared, for example, by reaction of hydroxylamine with the corresponding free hydrocarbyldicarboxylic acids which donate the hydrocarbyldicarbonyl radical, or reactive derivatives thereof. Reactive derivatives are, for example, the corresponding dicarboxylic acid anhyctride, dicarboxylic acid diazide or dicarboxylic acid dihalide, in particular the corresponding dicarboxylic acid dichloride, or the corresponding inner dicarboxylic acid anhydride (the two carbonyl groups bonded via oxa), or reactive derivatives formed in situ, for example prepared as described above for compounds of the formula IX and X in the reaction with hydroxylamine. The reaction preferably takes place under conditions analogous to those described above for the reaction of the compounds of the formula IX and X. Transamination of the corresponding dicarboxylic acid diesters, such as dicarboxylic acid di-lower alkyl esters, for example dicarboxylic acid dimethyl or diethyl esters, with hydroxylamine is also possible.

Compounds of the formula V are commercially obtainable, are known or can be prepared by processes known per se.

For example, compounds of the formula V can be prepared by abovementioned processes from compounds of the formula VIII in which Y' is replaced by hydrogen and the other radicals are as defined, or by reaction of analogues of compounds of the formula VII defined above, in which Y is replaced by a hydrogen atom, under the conditions mentioned for reduction and cleavage of the amide bond in compounds of the formula VII.

Compounds of the formula V,
in which

A is $C_3–C_6$cycloalkylene (in particular 1,3-cyclobutylene), m is 1 and n is 0 or 1, in particular 0;

with the provisos that a) the distance between the radical —$W_1^*$ (hydroxyl) and the radical $H_2N$— is at least 3 and not more than 4 carbon atoms and that b) the two radicals —$(CH_2)_m$—$W_1^*$ and $H_2N$—$(CH_2)_n$— are not bonded to the same ring carbon atom of A; are prepared, in particular, from compounds of the formula XI

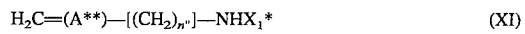

in which $A^{**}$ is $C_3–C_6$cycloalkan-1-yl-3-ylidene, in particular cyclobutan-1-yl-3-ylidene, n" is 0 or 1, in particular 0, and $X_i^*$ is tert-lower alkoxycarbonyl, such as tert-butoxycarbonyl, or phenyl-1-lower alkoxycarbonyl, such as benzyloxycarbonyl, with the provisos that a) the distance between the radical $H_2C$=(methylidene) and the radical $X_1^*HN$— is at least 2 and not more than 3 carbon atoms and that b) the two radicals $H_2C$=and $X_1^*HN$—$[(CH_2)_{n''}]$— are not bonded to the same ring carbon atom of A; by hydroboronation, preferably with $BH_3$ in an ether, such as tetrahydrofuran, with sodium borohydride and boron trifluoride-etherate in diethylene glycol dimethyl ether, or with sodium borohydride in the presence of a lower alkanoic acid, such as acetic acid, in an ether, such as tetrahydrofuran, at temperatures of between 0° and 40° C., in particular between 0° C. and room temperature, and subsequent alkaline oxidation, preferably with an aqueous solution of an ammonium or alkali metal hydroxide, such as sodium hydroxide or potassium hydroxide, and hydrogen peroxide at temperatures of between 0° and 50° C., in particular between 15° and 30° C., the methylidene group being converted into a hydroxymethyl radical and $X_1^*$ being split off simultaneously. In a preferred embodiment, $X_1^*$ is not split off and a compound of the formula III in which $X_1$ is replaced by the radical $X_1^*$ as defined last and $X_2$ is replaced by hydrogen, while the other radicals are as defined for compounds of the formula III, is obtained.

Compounds of the formula XI in which the radicals are as defined, in particular $A^{**}$ is cyclobutan-1-yl-3-ylidene and n" is 0 or 1, in particular 0, are prepared, for example, from carboxylic acids of the formula XII

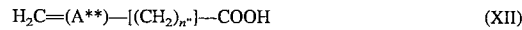

in which $A^{**}$ is $C_3–C_6$cycloalkan-yl-ylidene, in particular cyclobutan-1-yl-3-ylidene, and n is 0 or 1, in particular 0, with the provisos that a) the distance between the radical $H_2C=$ (methylidene) and the radical —COOH is at least 2 and not more than 3 carbon atoms and that b) the two radicals $H_2C=$ and $HOOC—[(CH_2)_{n''}]—$ are not bonded to the same ring carbon atom of A; by conversion of carboxylic acids of the formula XII, or of activated acid derivatives thereof, such as acid halides or anhydrides with lower alkanoic acids, such as acetic acid (which can be prepared by known processes), with an azide salt, for example an alkali metal azide, such as sodium azide, into the acid azide and reaction thereof (preferably under reflux) in a tertiary lower alkanol, such as tert-butanol, or a phenyl-1-lower alkanol, such as benzyl alcohol; preferably with direct preparation of acid azide in situ by reaction with an azide of an organic phosphoric acid azide, such as diphenylphosphoryl azide, in the alcohols mentioned under reflux; with rearrangement and formation of the radical $X_1$* (analogously to the Curtius degradation). The compounds of the formula XII are known or can be prepared by processes known per se, for example by a method analogous to that of Cripps, H. N., et al. in J. Am. Chem. Soc. 81, 2723–28 (1959).

Compounds of the formula V
in which
$W_1$* is hydroxyl,
A is $C_3$–$C_6$cycloalkylene, in particular 1,3-cyclobutylene,
n is 1 and
m is 0,
with the abovementioned provisos, can also be prepared from keto-nitrile compounds of the formula XIII

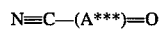  (XIII)

in which
A*** is $C_3$–$C_6$cycloalkan-yl-ylidene, such as cyclobutan-1-yl-3-ylidene,
with the provisos that a) the distance between the cyano radical and the oxo radical (=O) is at least 2 and not more than 3 carbon atoms and that b) the two radicals oxo and $N\equiv C—$ are not bonded to the same ring carbon atom of A; by simultaneous or stepwise reduction of the cyano and the keto group, for example first reduction of the keto group with a suitable complex hydride, such as lithium aluminium hydride (also allows simultaneous reduction of the cyano group), $LiAlH[OC(CH_3)_3]_3$ or bis(3-methyl-but-2-yl)borane (disiamylborane) in an ether, such as diethyl ether or tetrahydrofuran; or, in particular, with sodium borohydride or sodium cyanoborohydride, if appropriate in the presence of LiCl, in water or an alcohol, such as a lower alkanol or lower alkanediol, such as methanol, ethanol or ethylene glycol; at temperatures of between 0° and 50° C., for example between 25° and 40° C.; and (if necessary) subsequent reduction of the cyano group, for example by hydrogenation in the presence of a suitable heavy metal catalyst, in particular Raney nickel, in an alcohol, for example methanol or ethanol, preferably in the presence of ammonia, for example 1 to 15% by weight of ammonia, at temperatures of between 0° and 50° C., for example between 25° and 40° C.

Ketonitriles of the formula XIII are known or can be prepared by processes known per se. For example, 3-oxo-cyclobutanecarbonitrile can be obtained from 3-methylenecyclobutanecarbonitrile in a mixture of water and an ether, such as diethyl ether, at temperatures of between 0° and 30° C., in particular between 5° and 10° C., by addition of osmium acid and slow addition of an alkali metal metaperiodate, such as sodium metaperiodate, preferably under an inert gas, such as nitrogen, filtration, washing with a water-immiscible organic solvent, such as a halo-lower alkane, for example chloroform, evaporation of the organic phase, dissolving of the residue in an ether, such as tetrahydrofuran, addition of mercury and silver carbonate, leaving to stand under reflux and protection from light, evaporation of the ether and distillation of the corresponding product of the formula XIII in the vacuum of an oil pump. 3-Methylenecyclobutanecarbonitrile can by obtained by cycloaddition of allene (propadiene) onto acrylonitrile (Cripps, H. N., et al. in J. Am. Chem. Soc. 81, 2723–28 (1959)).

Compounds of the formula V
in which
A is as defined for compounds of the formula I, in particular 1,2-cyclopropylene,
m is 1,
n is 1 and
$W_1$* is hydroxyl,
with the abovementioned provisos, can be prepared, for example, by a process in which a cyanocarboxylic acid ester of the formula XIV

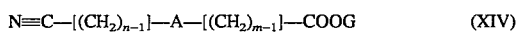  (XIV)

in which
A is as defined and
G is lower alkyl, such as methyl or ethyl, aryl, such as phenyl, naphthyl or fluoren-9-yl, or aryl-lower alkyl, such as phenyl-, naphthyl- or fluoren-9-ylmethyl and
n and m are as defined last,
with the proviso that the distance between the cyano radical and the radical —COOG is 2 carbon atoms; is converted into the corresponding compound of the formula V by simultaneous or stepwise reduction of the cyano and the keto group, for example first reduction of the ester group (—COOG) with a suitable complex hydride, such as lithium aluminium hydride (preferably; also allows simultaneous reduction of the cyano group) or $LiAlH[OC(CH_3)_3]_3$ in an ether, such as diethyl ether or tetrahydrofuran; or with sodium borohydride in the presence of LiCl in water or an alcohol, such as a lower alkanol or lower alkanediol, such as methanol, ethanol or ethylene glycol; at temperatures of between 0° C. and the reflux temperature, in particular at the reflux temperature; or with an alkali metal, such as sodium, in an alcohol, such as ethanol; and (if necessary) subsequent reduction of the cyano group, for example by hydrogenation in the presence of a suitable heavy metal catalyst, in particular Raney nickel, in an alcohol, for example methanol or ethanol, at temperatures of between 0° and 50° C., for example between 25° and 40° C.; or with hydrogenation, taking place in one batch, of the ester group to the hydroxymethyl group and of the cyano group to the aminomethyl group in the presence of a suitable catalyst, in particular a base heavy metal or an oxide thereof, such as nickel or cobalt (preferably nickel or Raney nickel in alcohols, such as ethanol, at temperatures of from 150° to 190° C. under increased pressure, for example under 50 to 200 bar), or noble metals or noble metal oxides, such as platinum, platinum oxide, palladium, palladium oxide or ruthenium (preferably in suitable solvents chosen from alcohols, such as methanol or ethanol, esters, such as ethyl acetate, and ethers, such as dioxane, or suitable mixtures of the solvents mentioned; preferably in the presence of an excess of ammonia, such as 1 to 15% by weight of ammonia, it also being possible for the catalysts mentioned to be bonded to suitable support materials, such as charcoal, barium sulfate or strontium sulfate, calcium carbonate, aluminium oxide or silica gel; at suitable temperatures, for example between 0° and 50° C., for example at room temperature; if necessary under increased pressure, for example under between 1 and 20 bar).

Compounds of the formula XIV are known or can be prepared by processes known per se. For example, a compound of the formula XIV
in which A is 1,2-cyclopropylene and G is ethyl (ethyl 2-cyanocyclopropanecarboxylate)

can be prepared by cycloaddition of ethyl diazoacetate ($N_2CH$—CO—OEt) onto acrylonitrile (for example in 2 to 3 times the molar amount with respect to ethyl dimacetate), preferably at elevated temperatures, in particular under reflux, distillation of excess acylonitrile and subsequent further heating to temperatures of between 120° and 170° C. The other starting materials are commercially obtainable, are known or can be prepared by processes known per se.

Additional process measures

Free compounds of the formula I obtainable by the processes defined and having salt-forming properties can be convened into their salts in a manner known per se; since these are basic compounds, this can be effected by treatment with acids or suitable derivatives thereof.

Furthermore, compounds of the formula II can be prepared from compounds of the formula I for purification purposes (for example for separation of protective diastereomers or of enantiomers with the aid of a protecting group with a centre of asymmetry which exists in the pure form (for example in the (S) or (R) configuration)). Liberation of the purified compounds of the formula I is then carried out by splitting off protecting groups as described above.

Isomer mixtures of compounds of the formula I which can exist in the form of several isomers can be separated into the individual isomers by processes known per se.

The cis or the trans isomer or both can be obtained in a pure form from mixtures of cis and trans isomers by customary processes. Suitable methods for removal of one isomer or for separation of the two isomers are, for example, chromatographic methods, for example adsorption chromatography on silica gel with elution with organic solvents or solvent mixtures, such as hydrocarbons, for example liquid lower alkanes, such as pentane, hexane or heptane, or esters, such as lower alkyl-lower alkanoates, for example ethyl acetate, or mixtures thereof, if necessary multiple partition between immiscible solvents, such as water and a water-immiscible organic solvent, for example a halogenated hydrocarbon, such as methylene chloride or chloroform, or fractional crystallization, for example from a solution in organic solvents, such as aromatics, for example benzene, toluene or xylene, if necessary with seeding with the pure cis or trans isomer.

Mixtures of enantiomers, for example, can be separated into individual enantiomers, preferably by formation of salts with optically pure salt-forming reagents, such as (S,S)- or (R,R)- tanaric acid, (R)- or (S)-lactic acid, 1(R)- or 1(S)- camphorsulfonic acid or (L)-glutamic acid, and separation of the diastereomer mixture thus obtainable, for example by means of fractional crystallization, and/or enantiomer separation by mechanical harvesting, by introduction of optically active protecting groups which have centres of asymmetry, such as (S)-1-phenylethyl, and separation of the resulting diastereomers, for example by fractional crystallization, preferably chromatographically, for example by partition or adsorption chromatography, or by partition in multi-phase solvent mixtures, and splitting-off of the protecting groups as described above, or by chromatography on optically active column materials, such as optically active quartz, cellulose, optically active ion exchangers, D-dinitrobenzoylphenylglycine covalently bonded to aminopropyl-silica gel (Pirkle phase), D-3,5-dinitrobenzoylphenylglycine bonded to silica gel, or an enantiomerically pure amino acid, such as (L)-valine or (L)-proline, covalently bonded to silica gel, if expedient and appropriate, also in the form of a copper complex.

Starting materials which allow selective preparation of individual isomers of the compounds of the formula I, for example pure cis or trans isomers or enantiomefically pure starting materials, in particular of the formula II, are preferably used directly. Salts of free compounds of the formula I can be prepared in a manner known per se, for example by treatment with an acid, such as an inorganic acid, for example hydrochloric acid or sulfuric acid, an organic carboxylic acid, for example adipic acid, or an organic sulfonic acid, for example benzenesulfonic acid, in a suitable solvent, for example water, an alcohol, such as methanol, an ether, such as diethyl ether, or mixtures thereof, or with a suitable artion exchanger reagent which is charged, for example, with the anion of the corresponding acid. Salts can be convened into the free compounds in the customary manner, for example by treatment with a suitable basic agent, such as a hydroxy base in free solution, for example an alkali metal hydroxide, or such as an anion exchanger charged with hydroxide, for example by chromatography or by the batch process.

The conversion of a salt of a compound of the formula I can be carried out by preparation of the free compound and subsequent conversion thereof into an acid addition salt, as just described.

Direct conversion of an acid addition salt of one of the compounds of the formula I and an acid into an acid addition salt of the compound of the formula I and another acid with the second; new acid is also possible. This conversion is preferably carried out a) by reaction of the original acid addition salt in free solution in the presence of a suitable amount of the new acid, for example an excess, or b) on an anion exchanger charged with the anion of the new acid.

Gel chromatography salt conversion processes can also be used for all reactions which serve to convert acid addition salts of bases of the formula I into other acid addition salts or into the free compounds or the free bases into the corresponding acids.

The conversion of a free compound or a salt, preferably a halide, such as chloride, into another salt, for example a halide, such as chloride, in the case of the free compound or a salt of a doubly negatively charged acid, for example a sulfate, in the case of the free compound or a salt is to be preferred, in particular, if a crystalline salt of a compound of the formula I is thus obtained.

General definition of the reaction conditions

As a result of the close relationship between starting materials with salt-forming groups in the free form and in the form of salts and also as a result of the close relationships between compounds of the formula I in the free form and in the form of salts, the corresponding free compounds or their salts above and below are also to be understood, where expedient and appropriate, as meaning the corresponding salts or free starting materials or compounds of the formula I.

If there are acid groups in the starting materials, for example sulfo or carboxyl groups, for example, salts with bases, for example metal salts, such as alkali metal or alkaline earth metal salts, for example sodium, potassium, magnesium or calcium salts, ammonium salts and salts with nitrogen bases, such as quaternary nitrogen compounds, for example tetra-lower alkylammonium compounds, and the like, can exist. If basic groups are present, for example, acid addition salts can exist analogously to those mentioned in the definition of salts of the compounds of the formula I.

The compounds according to the invention with their salt-forming basic groups can be obtained in the free form or in the form of salts, depending on the procedure and reaction conditions.

The compounds, including their salts, can also be obtained in the form of their hydrates, or their crystals can include, for example, the solvent used for the crystallization. Hydrates can also first be formed from the resulting compounds, for example by leaving them to stand in air.

Functional groups which are not intended to participate in the reaction, in particular amino and hydroxyl groups, are present in the starting materials, if necessary, in protected form. Protecting groups, in particular amino- and hydroxyl-protecting groups, are introduced into the starting materials (for example of the formula III) by methods known per se if necessary. Examples of suitable reaction conditions are described, for example, in the standard works by J. F. W. McOmie, "Protective Groups in Organic Chemistry", Plenum Press, London, New York, 1973, and T. W. Greene, "Protective Groups in Organic Synthesis", Wiley, New York, 1984. Amino groups to be protected can be protected simultaneously by two protecting groups only within the context of that possible chemically. Preferably, only one monovalent or only one bivalent protecting group is present in a protected amino group.

The protected intermediates which can be obtained can be liberated or can be used further without splitting off the protecting group. The introduction, the nature of the protecting groups used and their elimination here are analogous to those described above or below. If a centre of asymmetry exists in a protecting group and this radical is enantiomerically pure, for example in (S)-phenyl-lower alkyl-methyl, such as 1 (S)-phenyl-ethyl, corresponding diastereomers of intermediates can be used in order to obtain enantiomerically pure intermediates or enantiomerically pure compounds of the formula I by separation of these diastereomers, for example by means of chromatography on silica gel using organic solvent mixtures, such as (benzene or toluene)/(diethyl ether or dioxane)/(di-lower alkyl ketone, such as acetone).

If necessary, hydroxyl groups, for example hydroxyl $W_1$, can be present in protected form; like the amino-protecting groups already mentioned, the corresponding protecting groups can be mono- or bivalent (in the latter case, hydroxyl and amino can also be protected together, i.e., for example, one or two of the amino-protecting groups $X_1$, $X_2$, $X_3$ and $X_4$ each can protect a hydroxyl group with their second bond).

A hydroxyl group can be protected, for example, by a monovalent protecting group, such as an acyl group, for example lower alkanoyl which is unsubstituted or substituted by halogen, such as chlorine, such as acetyl or 2,2-dichloroacetyl, or in particular by an acyl radical of a carbonic acid half-ester mentioned for protected amino groups. A preferred hydroxyl-protecting group is, for example, 2,2,2-trichloroethoxycarbonyl, 4-nitrobenzyloxycarbonyl or diphenylmethoxycarbonyl. A hydroxyl group furthermore can be protected by tri-lower alkylsilyl, for example trimethylsilyl, triisopropylsilyl, tert-butyl-dimethylsilyl or, in particular, dimethyl-(2,3-dimethyl-2-butyl)silyl (=thexyldimethylsilyl), an etherifying group which can easily be split off, for example an alkyl group, such as tert-lower alkyl, for example tert-butyl, an oxa or a thia-aliphatic or -cycloaliphatic, in particular 2-oxa- or 2-thia-aliphatic or-cycloaliphatic, hydrocarbon radicals, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thiacycloalkyl having 5–7 ring atoms, such as 2-tetrahydrofuryl or 2-tetrahydropyranyl, or a corresponding thia analogue, and by 1-phenyl-lower alkyl, such as benzyl, diphenylmethyl or trityl, in which the phenyl radicals can be unsubstituted or substituted, for example by halogen, for example chlorine, lower alkoxy, for example methoxy, and/or nitro.

A hydroxyl and amino group occurring simultaneously in one molecule can be protected together, for example, by bivalent protecting groups, such as a methylene group which is unsubstituted or, preferably, substituted, for example by one or two lower alkyl radicals or oxo, for example by unsubstituted or substituted alkylene, for example lower alkylene, such as isopropylene, cycloalkylene, such as cyclohexylene, a carbonyl group or phenylmethylene.

A protected hydroxyl group is preferably protected by lower alkoxycarbonyl or tri-lower alkylsilyl, in particular by trimethylsilyl, tert-butyl-dimethylsilyl, dimethyl-(2,3-dimethyl-2-butyl)silyl or tert-butoxycarbonyl.

A hydroxyl group protected by a suitable acyl group or by unsubstituted or substituted 1-phenyl-lower alkyl is liberated analogously to a correspondingly protected amino group. A hydroxyl group protected by 2,2-dichloroacetyl is liberated, for example, by basic hydrolysis, and a hydroxyl group protected by tert-lower alkyl or by a 2-oxa- or 2-thia-aliphatic or-cycloaliphatic hydrocarbon radical is liberated by acidolysis, for example by treatment with a mineral acid or a strong carboxylic acid, for example trifluoroacetic acid.

A hydroxyl and amino group occurring simultaneously in a molecule which are protected together by means of a bivalent protecting group, preferably, for example, a methylene group mono- or disubstituted by lower alkyl, such as by lower alkylene, for example isopropylene, cycloalkylene, for example cyclohexylene, or phenylmethylene, can be liberated by acid solvolysis, in particular in the presence of a mineral acid or a strong organic acid.

Tri-lower alkylsilyl, such as trimethylsilyl or dimethyl-(2,3-dimethyl-2-butyl)silyl, is preferably split off by solvolysis, for example with alcohols, such as methanol or ethanol, at temperatures of between 20° C. and the reflux temperature. A tri-lower alkylsilyl group is also split off by acidolysis with a mineral acid, in particular hydrofluoric acid, or a strong carboxylic acid, or by reaction with the fluoride salt of a metal or a base which liberates fluoride ions, for example the acid addition salt of hydrogen fluoride and a nitrogen base or a metal fluoride, such as an alkali metal fluoride, for example sodium fluoride or potassium fluoride, in the absence or presence of a macrocyclic polyether ("crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of aprotic, polar solvents, such as ethers, for example tetrahydrofuran or dioxane, dimethylsulfoxide or N,N-dimethylacetamide, at preferred temperatures of about −20° to 50° C., for example at between 0° C. and room temperature.

2-Halo-lower alkoxycarbonyl as the hydroxyl-protecting group is removed by reducing agents, for example reducing metal, such as zinc, reducing metal salts, such as chromium(II) salts, or by sulfur compounds, for example sodium dithionite or, preferably, sodium sulfide and carbon disulfide.

Esterified hydroxyl groups, for example lower alkanoyloxy, such as acetyloxy, can also be liberated by esterases.

Hydroxyl groups can also be protected merely for the purpose of separating cis and trans compounds, for example of the formula III, from one another. This is effected, in particular, by introduction of a tri-lower alkylsilyl protecting group into a compound of the formula III under the conditions mentioned for introduction of corresponding protecting groups into compounds of the formula V. After subsequent separation of the cis/trans isomers, for example by chromatography, preferably on silica gel using suitable solvents or solvent mixtures as eluting agents, the hydroxyl-protecting groups are split off again from the separated isomers, as described above.

The abovementioned reactions can be carded out under reaction conditions known per se, in the absence (if the reagents, for example, themselves serve as solvents or are present as melts) or, usually, presence of solvents or diluents, preferably those which are inert towards the reagents used and dissolve or suspend these, in the absence or presence of catalysts, condensing agents or neutralizing agents, and, depending on the nature of the reaction and reaction participants, at reduced, normal or increased temperature, for example in the temperature range from about −80° C. to about 200° C., preferably about −20° C. up to the reflux temperature, for example at about 0° to 30° C. or at the reflux temperature, under atmospheric pressure or in a closed vessel, if appropriate under pressure, or in an inert atmosphere, for example under an argon or nitrogen atmosphere, if necessary with exclusion of light, the suitable parameters being chosen from those mentioned, where expedient and appropriate. The particular reaction conditions stated specifically are preferred.

Solvents and diluents are, for example, water, alcohols, for example lower alkyl hydroxides, such as methanol, ethanol or propanol, diols, such as ethylene glycol, triois, such as glycerol, or arylalcohols, such as phenol, acid amides, for example carboxylic acid amides, such as dimethylformamide or dimethylacetamide, or amides of inorganic acids, such as hexamethylphosphoric acid triamide or 1,3-dimethyl-3,4,5,6-tetrahydro-2(1H)-pyrimidinone (DMPU), ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as lower alkyl lower alkanoates, for example ethyl acetate, bisalkanesulfines, such as dimethyl sulfoxide, nitrogen heterocyclic compounds, such as pyridine, hydrocarbons, for example lower alkanes, such as heptane, or aromatics, such as benzene, toluene or xylene(s), or mixtures of these solvents, it being possible for the particular suitable solvents to be chosen for the abovementioned reactions.

Customary processes are used for working up the compounds of the formula I which are obtainable or their salts, for example solvolysis of excess reagents; recrystallization; chromatography, for example partition, ion or gel chromatography; partition between an inorganic and organic solvent phase; single or multiple extraction, in particular after acidification or increasing the basicity or the salt content; drying over hygroscopic salts; digestion; filtration; washing; dissolving; evaporation (if necessary in vacuo or under a high vacuum); distillation; crystallization, for example of resulting compounds in the form of an oil or from the mother liquor, it also being possible for the product to be seeded with a crystal of the end product; or a combination of two or more of the working-up steps mentioned, which can also be employed repeatedly, and the like.

Starting materials and intermediates can be used in the pure form, for example after working up, as mentioned last, in the partly purified form or also, for example, directly as the crude product.

Isomers, for example cis/trans isomers or enantiomers, can be separated at any suitable stage in the syntheses of compounds according to the invention, whether at the stage of intermediates or at that of the end products. The methods used here are analogous to those described above under the Additional Process Measures or to those in the section here on General Reaction Conditions. It is also possible to employ only isomerically pure starting materials directly.

Processes analogous to the processes mentioned in the examples are particularly preferred for the preparation both of the starting materials and of the end products.

The invention also relates to those embodiments of the process in which a compound obtainable as an intermediate at any process stage is used as the starting substance and the missing process steps are carried out, or in which a starting material is formed under the reaction conditions or is used in the form of a derivative, for example a salt thereof.

Pharmaceutical compositions

The present invention also relates to pharmaceutical compositions which comprise, as the active ingredient, one of the pharmacologically active compounds of the formula I or a pharmaceutically acceptable salt thereof. Compositions for enteral, in particular oral, and for parenteral administration are particularly preferred. The compositions comprise the active ingredient by itself or, preferably, together with a pharmaceutically acceptable carrier. The dosage of the active ingredient depends on the disease to be treated and on the species, age, weight, skin area and individual condition, as well as on the mode of administration.

The pharmaceutical compositions comprise about 5% to about 95% of the active ingredient, single-dose administration forms preferably containing about 20% to about 90% and administration forms which are not single-dosed preferably containing about 5% to about 20% of active ingredient. Dose unit forms, such as coated tablets, tablets or capsules, contain about 0.01 g to about 2 g, preferably about 0.05 g to about 1.0 g, of the active ingredient, in particular 0.1 to 0.6 g.

The present invention also relates to the use of compounds of the formula I for the preparation of pharmaceutical compositions for use as ODC inhibitors, for example for the treatment of diseases which respond to inhibition of ODC, in particular of the abovementioned diseases.

The pharmaceutical compositions of the present invention are prepared in a manner known per se, for example by means of conventional mixing, granulating, coating, dissolving or lyophilizing processes. Thus, pharmaceutical compositions for oral use can be obtained by combining the active ingredient with one or more solid carriers, granulating a resulting mixture, if appropriate, and processing the mixture or granules, if desired, to tablets or coated-tablet cores, if appropriate by addition of additional excipients.

Suitable careers are, in particular, fillers, such as sugars, for example lactose, sucrose, mannitol or sorbitol, cellulose preparations and/or calcium phosphates, for example tricalcium phosphate or calcium hydrogen phosphate, and furthermore binders, such as starches, for example corn, wheat, rice or potato starch, methylcellulose, hydroxypropylmethylcellulose, sodium carboxymethylcellulose and/or polyvinylpyrrolidone, and/or, if desired, disintegrants, such as the abovementioned starches, and furthermore carboxymethyl starch, crosslinked polyvinylpyrrolidone, alginic acid or a salt thereof, such as sodium alginate.

Additional excipients are, in particular, flow conditioners and lubricants, for example silicic acid, talc, stearic acid or salts thereof, such as magnesium stearate or calcium stearate, and/or polyethylene glycol, or derivatives thereof.

Coated-tablet cores can be provided with suitable coatings, if appropriate resistant to gastric juice, the substances used being, inter alia, concentrated sugar solutions, which contain gum arabic, talc, polyvinylpyrrolidone, polyethylene glycol and/or titanium dioxide if appropriate, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated-tablet coatings, for example for identification or characterization of different active ingredient doses.

Pharmaceutical compositions which can be used orally are also dry-filled capsules of gelatin and soft, closed capsules of gelatin and a softener, such as glycerol or sorbitol. The dry-filled capsules can contain the active ingredient in the form of granules, for example mixed with fillers, such as corn starch, binders and/or lubricants, such as talc or magnesium stearate, and if appropriate stabilizers. In soft capsules, the active ingredient is preferably dissolved or suspended in suitable liquid excipients, such as fatty oils, paraffin oil or liquid polyethylene glycols, it also being possible to add stabilizers.

Further oral administration forms are, for example, syrups which are prepared in the customary manner and contain the active ingredient, for example, in suspended form and in a concentration of about 5% to 20%, preferably about 10%, or in a similar concentration which gives a suitable single dose, for example, when 5 or 10 ml are measured out. Further suitable forms are also, for example, pulverulent or liquid concentrates for preparation of shakes, for example in milk. Such concentrates can also be packed in single-dose amounts.

Pharmaceutical compositions which can be used rectally are, for example, suppositories, which comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are, in particular, aqueous solutions of an active ingredient in water-soluble form, for example a water-soluble salt, or aqueous injection suspensions which contain viscosity-increasing substances, for example sodium carboxymethylcellulose, sorbitol and/or dextran, and if appropriate stabilizers. The active ingredient can also be present here in the form of a lyophilisate, if appropriate together with excipients, and can be dissolved by addition of suitable solvents before parenteral administration.

Solutions such as are used, for example, for parenteral administration can also be used as infusion solutions.

The invention also relates to a method (process) for the treatment of the abovementioned disease states in warm-blooded animals, i.e. mammals, and in particular humans, preferably those warm-blooded animals which require such treatment. The compounds of the formula I of the present invention or their pharmaceutical salts, if salt-forming groups are present, are administered for this purpose for prophylaxis or treatment, and are preferably used in the form of pharmaceutical compositions, for example in an amount which is suitable for inhibition of ornithine decarboxylase and is active prophylactically or therapeutically against one of the diseases mentioned which respond to inhibition of ornithine decarboxylase, for example tumours or protozoa infections. For a body weight of about 70 kg, a daily dose of about 0.3 g to about 15 g, preferably about 0.5 g to about 5 g, of a compound of the present invention is administered here.

The pharmaceutical compositions are preferably those which are suitable for administration to a warm-blooded animal, for example a human, for treatment or prophylaxis of one of the abovementioned diseases which responds to inhibition of ornithine decarboxylase and comprise an amount of a compound of the formula I or of a pharmaceutically acceptable salt thereof which is active against diseases which respond to inhibition of ornithine decarboxylase (in particular an amount which is active for inhibition of this enzyme ), together with an excipient.

The examples described below serve to illustrate the invention, without limiting the scope thereof.

The abbreviation BOC represents the tert-butoxycarbonyl group. m.p. is "melting point", decomp. is "with decomposition ". Brine is sodium chloride solution which is saturated at room temperature. Temperatures are stated in degrees Celcius. The $R_f$ values (ratio of the migration zone covered by the compound to be determined to the zone covered by the solvent front) are stated for thin layer chromatography. In the case of mixtures of solvents and diluents, the volume ratios are stated.

EXAMPLE 1 trans-4-Aminooxy-cyclohexylamine dihydrochloride

A mixture of 8.77 g (0.0381 mol) of trans-(4-aminooxy)-N-BOC-cyclohexylamine and 180 ml of 3.5M methanolic hydrochloric acid is stirred at room temperature for 3 hours and then evaporated in vacuo. The residue is taken up in methanol and the mixture is evaporated again in vacuo. Recrystallization of the residue from methanol/diethyl ether gives the title compound, m.p. >260° C. (brown discoloration above 230° C.).

The starting compounds are prepared as follows:
a) trans-(4-Aminooxy)-N-BOC-cyclohexylamine A mixture of 16.2 g (0.04495 mol) of 2-[trans-4-(N-BOC-amino)-cyclohexyloxy]- 1H-iso-indole-1,3(2H)-dione and 95 ml of hydrazinc hydrate is stirred at room temperature for ½ hour, 145 ml of water are then added and stirring is continued for ½ hour. After addition of 450 ml of diethyl ether, the reaction mixture is stirred for a further 2 hours and the ether phase is then separated off. The aqueous phase is extracted three times with 200 ml of diethyl ether each time. The combined ether phases are washed with brine, dried over sodium sulfate and evaporated in vacuo, the title compound being obtained in crystalline form, m.p. 105°–106° C.
b) 2-[trans-4-(N-BOC-amino)-cyclohexyloxy]-1H-isoindole-1,3(2H)-dione A solution of 12 ml (0.0718 mol) of diethyl azodicarboxylate (93%) in 80 ml of benzene is added dropwise to a mixture of 14.62 g (0.06791 mol) of cis-4-(N-BOC-amino)-cyclohexanol, 11.1 g (0.068 mol) of N-hydroxyphthalimide, 17.84 g (0.068 mol) of triphenylphosphine and 600 ml of benzene at 20°–30° C., while stirring. The reaction mixture is further stirred at room temperature for 15 hours and then evaporated in vacuo. The residue is purified by flash chromatography on silica gel of particle size 0.04–0.063 mm using methylene chloride. After evaporation of the product-containing fractions, the title compound is obtained as a crystalline residue, m.p. 207°–208° C.

c) cis-4-(N-BOC-amino)-cyclohexanol and trans-4-(N-BOC-amino)-cyclohexanol

A solution of 51.73 g (0.237 mol) of di-tert-butyl-dicarbonate in 100 ml of tetrahydrofuran is added dropwise to a solution of 52 g (0.2257 mol) of 4-amino-cyclohexanol (Fluka, Buchs, Switzerland; cis/trans mixture; 50% in water) in 100 ml tetrahydrofuran and the mixture is stirred at room temperature for 15 hours. The reaction mixture is then evaporated to dryness in vacuo and the residue is stirred in 300 ml of diethylether. After filtration and washing of the crystals with diethylether, the trans title compound is obtained, m.p. 166° C. [cf. Anti-Cancer Drug Design 2, 25 (1987)]. The filtrate is evaporated in vacuo and the residue is purified by means of flash chromatography on silica gel using ethyl acetate/hexane mixtures (1:2 and 1:1). The cis title compound is thus obtained, m.p. 92°–94° C.

EXAMPLE 2 cis-4-Aminooxy-cyclohexylamine dihydrochloride

Analogously to Example 1, starting from 0.875 g (0.0038 mol) of cis-(4-aminooxy)-N-BOC-cyclohexylamine and 10 ml of 3M methanolic hydrochloric acid, but maintaining a reaction time of 20 hours, the title compound is obtained, m.p. 196°–197° C. (decomp.).

The starting compounds are prepared as follows:

a) cis-(4-Aminooxy)-N-BOC-cyclohexylamine

A mixture of 2 g of (0.00555 mol) of 2-[cis-4-(N-BOC-amino)-cyclohexyloxy]- 1H-iso-indole-1,3(2H)-dione and 12 ml of hydrazine hydrate is stirred at room temperature for 1 hour, 50 ml of diethyl ether are then added and stirring is continued for 1.5 hours. The organic phase is then separated off and worked up analogously to Example 1a. The resulting crystalline title compound melts at 120°–121° C.

b) 2-[cis-4-(N-BOC-amino)-cyclohexyloxyl]-1H-isoindole-1,3(2H)-dione 4.1 ml (0.0244 mol) of diethyl azodicarboxylate (93%) are added dropwise to a mixture of 5 g (0.0232 mol) of trans-4-(N-BOC-amino)-cyclohexanol (cf. Example 1c), 3.8 g (0.0232 mol) of N-hydroxyphthalimide, 6.1 g (0.0232 mol) of triphenylphosphine and 100 ml of tetrahydrofuran at 20°–30° C. The reaction mixture is further stirred at room temperature for 15 hours and then evaporated in vacuo. To separate off the diethyl 1,2-hydrazinc dicarboxylate and triphenylphosphine oxide, the oily residue is dissolved in ethyl acetate, the solution is cooled to 0° C. and filtered, the filtrate is evaporated and the same operation is repeated once more, but using diethyl ether. The residue obtained after evaporation of the diethyl ether is purified by means of flash chromatography on silica gel using ethyl acetate/hexane mixtures (1:2 and 1:1). After evaporation of the product-containing fractions, the title compound is obtained as a crystalline residue, m.p. 134°–135° C.

EXAMPLE 3 trans-3-Aminooxy-cyclohexylamine dihydrochloride

A mixture of 4.5 g (0.0261 mol) of trans-(3-aminooxy)-N-acetyl-cyclohexylamine and 22 ml of 2M sodium hydroxide solution (0.044 mol) is heated under reflux for 15 hours, while stirring. The reaction mixture is cooled and extracted thoroughly with methylene chloride, and the organic phase is dried over sodium sulfate and evaporated in vacuo. The oily residue is dissolved in a little methanol, a slight excess of 2M methanolic hydrochloric acid is added and the mixture is evaporated in vacuo. After recrystallization of the residue from methanol/diethyl ether, the title compound is obtained, m.p. 190° C. (decomp.).

The starting compounds are prepared as follows:

a) trans-(3-Aminooxy)-N-acetyl-cyclohexylamine

A mixture of 13.4 g (0.0443 mol) of 2-[trans-3-(acetamino)-cyclohexyloxy]- 1H-iso-indole-1,3(2H)-dione and 70 ml of hydrazine hydrate is stirred at room temperature for 1 hour. After addition of 250 ml of diethyl ether, stirring is continued at room temperature for a further 2 hours, the organic phase is then separated off and the hydrazine hydrate phase is evaporated in vacuo. 500 ml of ethanol are added to the residue. The mixture is heated to the reflux temperature, allowed to cool to room temperature and filtered and the filtrate is evaporated in vacuo. The residue is purified by means of flash chromatography on silica gel using methylene chloride/methanol mixtures (50:1 and 9:1). After evaporation of the product-containing fractions and recrystallization of the residue from methanol/diethyl ether, the title compound is obtained, m.p. 95°–96° C.

b) 2-[trans-3-(Acetamino)-cyclohexyloxy]-1H-isoindole-1,3(2H)-dione and 2-[cis-3acetamino)-cyclohexyloxyl]-1H-isoindole-1,3(2H)-dione 46 ml (0.275 mol) of diethyl azodicarboxylate (93%) are added dropwise to a mixture of 39.3 g (0.25 mol) of 3-acetaminocyclohexanol [cf. J. Am. Chem. Soc. 75, 1345 (1953)], 40.78 g (0.25 mol) of N-hydroxyphthalimide, 65.58 g (0.25 mol) of triphenylphosphine and 750 ml of tetrahydrofuran at 20°–30° C., and the reaction mixture is then stirred at room temperature for 15 hours. The product which has precipitated is filtered off, washed with tetrahydrofuran and recrystallized from ethanol. The trans title compound thus obtained melts at 214°–215° C.

To obtain the cis title compound, the filtrate and the mother liquor from the above recrystallization are combined and evaporated in vacuo and the residue is purified by means of flash chromatography on silica gel using toluene/isopropanol mixtures (97.5:2.5 and 19:1). After evaporation of the product-containing fractions, the cis title compound is obtained as a crystalline residue, m.p. 248°–249° C.

EXAMPLE 4 cis-3-Aminooxy-cyclohexylamine dihydrochloride

Analogously to Example 3, starting from 1.38 g (0.008 mol) of cis-(3-aminooxy)-N-acetyl-cyclohexylamine and 7 ml of 2M sodium hydroxide solution (0.014 mol), the title compound is obtained, m.p. 193°–194° C. (decomp.).

The starting compound is prepared as follows:

a) cis-(3-Aminooxy)-N-acetyl-cyclohexylamine

A mixture of 3.02 g (0.01 mol) of 2-[cis-3-(acetamino)-cyclohexyloxy]-1H-isoindole-1,3(2H)-dione (cf. Example 3b), 0.52 ml of hydrazine hydrate (0.0105 mol) and 60 ml of ethanol is boiled under reflux for 1 hour, while stirring. The mixture is cooled to room temperature and filtered, the filtrate is evaporated in vacuo and the residue is purified by means of flash chromatography on silica gel using methylene chloride/methanol mixtures (50:1 and 50:3). After evaporation of the product-containing fractions, the title compound is obtained as an oil which gradually solidifies as crystals, m.p. 94°–96° C.

EXAMPLE 5 cis-3-Aminooxymethyl-cyclopentylamine dihydrochlofide

A mixture of 2 g (0.00555 mol) of 2-[cis-3-(N-BOC-amino)-cyclopentylmethoxy]- 1H-iso-indolc-1,3(2H)-dione and 8 ml of hydrazinc hydrate is stirred at room temperature for ½ hour, 25 ml of diethyl ether are then added and stirring is continued for ½ hour. The organic phase is separated off and the hydrazinc hydrate phase is extracted thoroughly with diethyl ether. The combined ether phases are washed with water and brine, dried over sodium sulfate and evaporated in vacuo. 25 ml of 3M methanolic hydrochloric acid are added to the crude cis-3-aminoxymethyl-N-BOC-cyclopentylamine thus obtained, $R_f$ value =0.15 (silica gel/ethyl acetate:hexane (2:1)) and the reaction mixture is stirred at room temperature for 15 hours. After evaporation in vacuo and recrystallization of the residue from ethanol/diethyl ether, the title compound is obtained, m.p. 137° C. (decomp.).

The starting compounds are prepared as follows:
a) 2-[cis-3-(N-BOC-amino)-cyclopentylmethoxv]-1H-isoindole-1,3(2H)-dione A solution of 2.94 ml (0.01755 mol) of diethyl azodicarboxylate (93%) in 10 ml of benzene is added dropwise to a mixture of 3.6 g (0.01672 mol) of cis-3-(N-BOC-amino)-cyclopentanemethanol, 2.73 g (0.01673 mol) of N-hydroxyphthalimide, 4.49 g (0.01672 mol) of triphenylphosphine and 60 ml of benzene at 20°–30° C., while stirring. After the mixture has been stirred at room temperature for 1 hour, the precipitate formed during the reaction is filtered off, the residue on the filter is suspended in benzene and the suspension is filtered again. The latter operation is repeated twice more (residue on the filter: diethyl 1,2-hydrazinedicarboxylate), and the resulting filtrates are combined and these are evaporated in vacuo. Purification of the residue is carried out by means of flash chromatography on silica gel using ethyl acetate/hexane mixtures (1:3 and 1:1). The title compound is thus obtained, m.p. 162°–163° C.
b) cis-3-(N-BOC-amino)-cyclopentanemethanol 2.7 g (0.0714 mol) of sodium borohydride are added in portions to a solution of 3.8 g (0.018 mol)of N-BOC-2-azabicyclo[2.2.1]heptan3-one in 125 ml of methanol in the course of 20 minutes, while stirring and cooling in an ice-bath. The reaction mixture is further stirred at 0° C. for 1 hour and at room temperature for 1 hour, a solution of 4.08 ml (0.0714 mol) of acetic acid in 8 ml of methanol is then added dropwise and the mixture is evaporated to dryness in vacuo. The crystalline residue is partitioned between methylene chloride and water. After the organic phase has been washed with brine, dried over sodium sulfate and evaporated in vacuo, the title compound is obtained as crystalline residue, m.p. 73°–74° C.
c) N-BOC-2-Azabicyclo[2.2.1]heptan-3-one 0.019 g (0.00075 mol) of 4-dimethylamino-pyridine is added to a solution of 5.56 g (0.05 mol) of 2-azabicyclo [2.2.1]heptan-3-one [J. Ore. Chem. 39, 564 (1974)]and 12 g (0.055 mol) of di-tert-butyl dicarbonate in 50 ml of tetrahydrofuran and the mixture is stirred at room temperature for 15 hours. It is then evaporated in vacuo and the residue is recrystallized from ethyl acetate/hexane. The title compound thus obtained melts at 89°–90° C.

EXAMPLE 6 cis-3-Aminooxymethyl-cyclobutylamine dihydrochlofide

A mixture of 10.3 g (0.02973 mol)of 2-[cis-3-(N-BOC-amino)-cyclobutylmethoxy]- 1H- isoindole-1,3(2H)-dione, 54 ml of water and 45 ml of concentrated (approximately 12M) hydrochloric acid is heated under reflux for 1.5 hours. The reaction mixture is then cooled to 0° C. and filtered, the residue on the filter (phthalic acid) is washed with water and the filtrate is evaporated in vacuo. The residue is dissolved in ethanol and the solution is evaporated again in vacuo. After recrystallization of the residue from methanol/diethyl ether, the title compound is obtained, m.p. 192° C. (decomp.).

The starting compounds are prepared as follows:
a) 2-[cis-3-(N-BOC-amino)-cyclobutylmethoxyl]-1H-isoindole-1,3(2H)-dione A solution of 6.54 ml (0.0391 mol) of diethyl azodicarboxylate (93%) in 30 ml of benzene is added dropwise to a mixture of 7.5 g (0.03726 mol) of cis-3-(N-BOC-amino)-cyclobutanemethanol, 6.08 g (0.03726 mol) of N-hydroxyphthalimide, 9.774 g (0.03726 mol) of triphenylphosphine and 120 ml of benzene at 20°–30° C., while stirring. The reaction mixture is stirred at room temperature for 2 hours and filtered, the crystalline residue (diethyl 1,2-hydrazinedicarboxylate) is washed with benzene and the filtrate is evaporated in vacuo. The residue is purified by means of flash chromatography on silica gel using ethyl acetate/hexane mixtures (1:3 and 1:2). After evaporation of the product-containing fractions and recrystallization of the residue from ethyl acetate/hexane, the title compound is obtained, m.p. 131.5°–132.5° C.
b) cis-3-(N-BOC-amino)-cyclobutanemethanol 98.95 ml (0.09895 mol) of a 1M tetrabutylammonium fluoride solution in tetrahydrofuran are added dropwise to a solution of 17 g (0.04947 mol) of cis-3-(N-BOC-amino)-1-(thexyl-dimethylsilyl)oxymethyl-cyclobutane (-thexyl- =-2,3-dimethyl-2-butyl-) in 75 ml of tetrahydrofuran, while stirring and cooling in an ice-bath. The reaction mixture is further stirred at room temperature for 1.5 hours, 150 ml of brine are then added and the mixture is extracted 5 times with 100 ml of ethyl acetate each time. After the combined organic phases have been washed with 100 ml of brine and evaporated in vacuo, the residue is purified by means of flash chromatography on silica gel using ethyl acetate/hexane mixtures (1:2 and 1:1). The product-containing fractions are evaporated and the residue is recrystallized from diisopropyl ether. The title compound is thus obtained, m.p. 83°–84° C.
c) cis-3-(N-BOC-amino)-1-(thexyl-dimethylsilyl)oxymethyl-cyclobutane and trans-(N-BOC-amino)-1-(thexyl-dimethylsilyl)oxymethyl-cyclobutane 49.18 ml (0.2495 mol) of thexyldimethylchlorosilane are added dropwise to a solution of 45.65 g (0.2268 mol) of 3-(N-BOC-amino)-cyclobutanemethanol (EP 0 366 059 A2) and 40.55 ml (0.2723 mol) of 1,8-diazabicyclo[5.4.0]undec-7-ene in 400 ml of acetonitrile at 20°–25° C., while stirring. The reaction mixture is further stirred at room temperature for 15 hours and then evaporated in vacuo. The residue is partitioned between methylene chloride and water, the organic phase is dried over sodium sulfate and evaporated and the oily residue is purified by means of flash chromatography on silica gel using hexane and hexane/ethyl acetate mixtures (49:1 and 19:1 and 12.5:1). The product-containing fractions are evaporated, the cis title compound, $R_f$ value=0.25 (silica gel/ethyl acetate:hexane (1:15)) and the trans title compound, $R_f$ value=0.23, being obtained as oils.

EXAMPLE 7 trans-3-Aminooxymethyl-cyclobutylamine dihydrochloride

Analogously to Example 6, starting from 7.25 g (0.02093 mol) of 2-[trans-3-(N-BOC-amino)-cyclobutylmethoxy]-1H-isoindole-1,3(2H)-dione, 35 ml of water and 30 ml of concentrated hydrochloric acid, the title compound is obtained, m.p. 198° C. (decomp.).

The starting compounds are prepared as follows:
a) 2-[trans-3-(N-BOC-amino)-cyclobutylmethoxy]-1H-isoindole-1,3(2H)-dione Analogously to Example 6a, starting from 5.6 g (0.02782 mol) of trans-3-(N-BOC-amino)-cyclobutanemethanol, 4.54 g (0.02783 mol) of N-hydroxyphthalimide, 7.3 g (0.02783 mol) of triphenylphosphine and 5.12 ml (0.0306 mol) of diethyl azodicarboxylate (93%), the title compound is obtained, m.p. 120°–122° C.

b) trans-3-(N-BOC-amino)-cyclobutanemethanol

Analogously to Example 6b, starting from a solution of 13.2 g (0.03842 mol) of trans3-(N-BOC-amino)-1-(thexyldimethylsilyl)oxymethyl-cyclobutane (cf. Example 6c) in 60 ml of tetrahydrofuran and 76.8 ml (0.0768 mol) of a 1M tetrabutylammonium fluoride solution in tetrahydrofuran, the title compound is obtained, m.p. 98°–100° C.

The title compound 7b can also be obtained as follows:

A solution of 10 g of 3-(N-BOC-amino)-cyclobutanemethanol [cis/trans mixture (cf. EP 0 366 059 A2)]in 20 ml of benzene and 30 ml of diisopropyl ether is seeded with a few crystals of trans-3-(N-BOC-amino)-cyclobutanemethanol at room temperature, while stirring slowly. The mixture is stirred for 15 hours and filtered and the crystals are washed with diisopropyl ether. The pure title compound is obtained by recrystallization of the crude product, which is still contaminated with only about 3% of cis-3-(N-BOC-amino)cyclobutanemethanol from diisopropyl ether, m.p. 98°–99° C.

EXAMPLE 8

3-Aminooxymethyl-cyclobutylamine dihydrochloride

Analogously to Example 6, starting from 1.15 g (0.00332 mol) of 2-[3-(N-BOC-amino)cyclobutylmethoxy] -1H-isoindole-1,3(2H)-dione, 6 ml of water and 5 ml of concentrated hydrochloric acid, the title compound is obtained, m.p. 179° C. (decomp.).

The starting compound is prepared as follows:

a) 2-[3-(N-BOC-amino)-cyclobutylmethoxy]-1H-isoindole-1,3(2H)-dione

Analogously to Example 6a, starting from 1.59 g (0.0079 mol) of 3-(N-BOC-amino)-cyclobutanemethanol (EP 0 366 059 A2), 1.29 g (0.0079 mol) of N-hydroxyphthalimide, 2.07 g (0.0079 mol) of triphenylphosphine and 1.39 ml (0.0083 mol) of diethyl azodicarboxylate (93%), the title compound is obtained, m.p. 108°–109° C.

EXAMPLE 9

3-Aminooxy-cyclobutylmethylamine dihydrochlofide

A mixture of 0.58 g (0.001674 mol) of 2-[3-(N-BOC-aminomethyl)-cyclobutyloxy]-1H-isoindole-1,3(2H)-dione, 3 ml of hydrazinc hydrate and 10 ml of diethyl ether is stirred at room temperature for ½ hour. The ethereal phase is separated off, 2 ml of water and 10 ml of diethyl ether are added to the hydrazine hydrate phase, the mixture is stirred at room temperature for ¼ hour and the organic phase is then separated off. After the last operation has been repeated, the combined ethereal phases are washed with water and brine, dried over sodium sulfate and evaporated in vacuo.

10 ml of 3M methanolic hydrochloric acid are added to the oily 3-aminooxy-N-BOC-cyclobutylmethylamine thus obtained, $R_f$ value=0.63 (silica gel/methylene chloride: methanol (9:1)), and the reaction mixture is stirred at room temperature for 15 hours. After evaporation in vacuo and recrystallization of the residue from methanol/diethyl ether, the title compound is obtained, m.p. 213° C. (decomp.).

The starting compounds are prepared as follows:

a) 2-[3-(N-BOC-aminomethyl)-cyclobutyloxy]-1H-isoindole-1,3(2H)-dione

Analogously to Example 1 b, but using ethyl acetate/hexane mixtures (1:3 and 1:1) in the flash chromatography, starting from 15.24 g (0.0757 mol) of 3-(N-BOC-aminomethyl)-cyclobutanol, 12.35 g (0.0757 mol) of N-hydroxyphthalimide, 19.85 g (0.0757 mol) of triphenylphosphine and 13.3 ml (0.0795 mol) of diethyl azodicarboxylate (93%), the title compound, which melts at 161°–162° C. after recrystallization from ethyl acetate, is obtained. Evaporation of the mother liquor and recrystallization of the residue from ethyl acetate/hexane gives a further batch of the title compound, m.p. 145°–150° C.

b) 3-(N-BOC-aminomethyl)-cyclobutanol

A solution of 59.2 g (0.2712 mol) of di-tert-butyldicarbonate in 100 ml of tetrahydrofuran is added dropwise to a suspension of 24.94 g (0.2466 mol) of 3-aminomethyl-cyclobutanol in 180 ml of tetrahydrofuran in the course of 1 hour. 80 ml of water are then added to the reaction mixture, stirring is continued at room temperature for a further 16 hours and the mixture is evaporated in vacuo. The title compound, obtained as a crystalline residue, melts at 96–°99° C.

c) 3-Aminomethyl-cyclobutanol

A mixture of 24.28 g (0.25 mol) of 3-cyano-cyclobutanol [J. Am. Chem. Soc. 93,110 (1971)], 550 ml of an approximately 8 % ethanolic ammonia solution and 10.9 g of Raney nickel is hydrogenated at 35° C. After the end of the uptake of hydrogen, the catalyst is filtered off and the filtrate is evaporated in vacuo. The title compound, obtained as a crystalline residue, melts at 72° C.

EXAMPLE 10 cis-2-Aminooxymethyl-cyclopropylmethylamine dihydrochloride

A mixture of 1.5 g (0.00433 mol) of 2-[cis-2-(N-BOC-aminomethyl)-cyclopropylmethoxy]-1H-isoindole-1,3(2H)-dione and 9 ml of hydrazinc hydrate is stirred at room temperature for ½ hour. 9 ml of water are then added to the reaction mixture and, after a further ½ hour, 50 ml of methylene chloride are added. The reaction mixture is further stirred for another 3 hours, the methylene chloride phase is then separated off and the aqueous phase is washed twice with 30 ml of methylene chloride each time. The combined organic phases are washed with brine, dried over sodium sulfate and evaporated. The oily cis-2-aminoxymethyl-N-BOC-cyclopropylmethylamine thus obtained, $R_f$ value=0.13 (silica gel/ethyl acetate:hexane (1:1)), is dissolved in 18 ml of 3M methanolic hydrochloric acid and the reaction mixture is stirred at room temperature for 1 hour. After addition of diethyl ether and cooling in an ice-bath, the title compound which has crystallized out is filtered off, washed with diethyl ether and dried, m.p. 178°–180° C. (decomp.).

The starting compounds are prepared as follows:

a) 2-[cis-2-(N-BOC-aminomethyl)-cyclopropylmethoxy]-1H-isoindole-1,3(2H)-dione

A solution of 2.61 ml (0.0157 mol) of diethyl azodicarboxylate (93%) in 15 ml of benzene is added dropwise to a mixture of 3 g (0.0149 mol) of cis-2-(N-BOC-aminomethyl)-cyclopropanemethanol, 2.43 g (0.0149 mol) of N-hydroxyphthalimide, 3.9 g (0.0149 mol) of triphenylphosphine and 120 ml of benzene at 20°–30° C., while stirring. The reaction mixture is stirred at room temperature for 16 hours and filtered, the crystalline residue is washed with benzene and the filtrate is evaporated in vacuo. The residue is purified by means of flash chromatography on silica gel using hexane and hexane/ethyl acetate (2:1). After evaporation of the product-containing fractions and crystallization of the residue from methanol/hexane, the title compound is obtained, m.p. 96°–97° C.

b) cis-2-(N-BOC-aminomethyl)-cyclopropanemethanol

A solution of 25.45 g (0.1166 mol) of di-tert-butyldicarbonate in 100 ml of tetrahydrofuran is added dropwise to a solution of 10.9 g (0.1078 mol) of cis-2-aminomethyl-cyclopropanemethanol [J. Meal. Chem. 31, 2304 (1988)] in 100 ml of tetrahydrofuran and the mixture is stirred at room temperature for 15 hours. The reaction mixture is then evaporated in vacuo and the residue is purified by means of flash chromatography on silica gel using ethyl acetate/hexane (1:1). After evaporation of the product-containing fractions, the title compound is obtained as a colourless oil, $R_f$ value=0.23 (silica gel/ethyl acetate:hexane (1:1)).

EXAMPLE 11 trans-2-Aminooxymethyl-cyclopropylmethylamine dihydrochloride

Analogously to Example 10, starting from 0.46 g (0.00133 mol) of 2-[trans-2-(N-BOC-aminomethyl)-cyclopropylmethoxy]-1H-isoindole-1,3(2H)-dione and 3 ml of hydrazinc hydrate, oily trans-2-aminooxymethyl-N-BOC-cyclopropylmethylamine is obtained, $R_f$ value=0.07 (silica gel/ethyl acetate:hexane (1:1)).

This is dissolved in 4.5 ml of 3M methanolic hydrochloric acid, and the reaction mixture is stirred at room temperature for ¼ hour. After evaporation and crystallization of the residue from ethanol/diethyl ether, the title compound is obtained, m.p. 175°–176° C. (decomp.).

The starting compounds are prepared as follows:
a) 2-[trans-2-(N-BOC-aminomethyl)-cyclopropylmethoxy]-1H-isoindole-1,3(2H)4-dione Analogously to Example 10a, starting from 2.0 g (0.00994 mol) of trans-2-(N-BOC-aminomethyl)-cyclopropanemethanol, 1.62 g (0.00994 mol) of N-hydroxyphthalimide, 2.61 g (0.00995 mol) of triphenylphosphine and 1.75 ml (0.01047 mol) of diethyl azodicarboxylate (93%), the title compound is obtained as a colourless resin, $R_f$ value= 0.36 (silica gel/ethyl acetate:hexane (1:1)).

b) trans-2-(N-BOC-aminomethyl)-cyclopropanemethanol

Analogously to Example 10b, starting from 11.69 g (0.1156 mol) of trans-2-amino-methyl-cyclopropanemethanol [J. Med. Chem. 31, 2304 (1988)] and 27.3 g (0.1251 mol) of di-tert-butyl-dicarbonate, the title compound is obtained in the form of an oil, $R_f$ value =0.16 (silica gel/ethyl acetate:hexane (1:1)).

EXAMPLE 12 trans-4-Aminooxy-cyclohexylamine dihydrochloride

A mixture of 19.65 g (0.1141 mol) of trans-(4-aminooxy)-N-acetyl-cyclohexylamine and 140 ml 15 % strength sodium hydroxide solution (0.525 mol) is heated at 100° C. for 8 hours, while stirring and under a nitrogen atmosphere. After working up analogously to Example 3, the title compound is obtained, m.p.>260° C.

The starting compounds are prepared as follows:
a) trans-(4-Aminooxy)-N-acetyl-cyclohexylamine A mixture of 37.4 g (0.1237 mol) of 2-[trans-4-(acetamino)-cyclohexyloxy]-1H-iso-indole-1,3(2H)-dione, 12.3 ml (0.248 mol) of hydrazine hydrate, 620 ml of ethanol and 225 ml of methylene chloride is heated under reflux for 1 hour. The mixture is cooled to room temperature and filtered, the residue on the filter is washed with methylene chloride and the filtrate is evaporated in vacuo. The crystalline residue is taken up in 200 ml of methylene chloride, insoluble constituents are filtered off and the filtrate is evaporated again in vacuo. The last operation is repeated once more using 250 ml of methylene chloride. The title compound is thus obtained as a crystalline residue, m.p. 105°–106° C.

b) 2-[trans-4-(Acetamino)-cyclohexyloxy]-1H-isoindole-1,3(2H)-dione

A solution of 39.5 ml (0.2413 mol) of diethyl azodicarboxylate (95%) in 300 ml of tetrahydrofuran is added dropwise to a mixture of 36.13 g (0.2298 mol) of cis-4-acetaminocyclohexanol [Ber. Dtsch. Chem. Ges. 72, 995 (1939)], 37.49 g (0.2298 mol) of N-hydroxyphthalimide, 60.28 g of triphenylphosphine and 1500 ml of tetrahydrofuran at 20°–30° C., while stirring. After stirring at room temperature for 14 hours, in each case 20% of the amount of triphenylphosphine and diethyl azodicarboxylate originally employed is again added to the reaction mixture, stirring is continued for 6 hours and the reaction mixture is left to stand at room temperature for 2.5 days. The crystalline precipitate formed is filtered off and washed with tetrahydrofuran. The title compound thus obtained melts at 210°–213° C. The yield can be increased by further recrystallization or chromatography of the mother liquor.

EXAMPLE 13

Capsules

Capsules containing 0.25 g of active ingredient, for example one of the compounds of Examples 1–12, can be prepared as follows:

| Composition (for 5000 capsules) | |
|---|---|
| Active ingredient | 1250 g |
| Talc | 180 g |
| Wheat starch | 120 g |
| Magnesium stearate | 80 g |
| Lactose | 20 g |

The pulverulent substances are forced through a sieve of mesh width 0.6 mm and mixed.

Gelatin capsules are filled with portions of 0.33 g each of the mixture by means of a capsule filling machine.

EXAMPLE 14

Pharmacological data:

On measurement of the $IC_{50}$ for inhibition of ornithine decarboxylase (by the abovementioned method of Seely and Pegg with ODC from rat liver (obtained by the method of Hayashi and Kameji, see above)) and of the $IC_{50}$ for inhibition of proliferation of T24 bladder carcinoma cells as described above, the following $IC_{50}$ values can be found with the particular compounds mentioned from the examples:

| Compound from Example | ODC inhibition $IC_{50}$ (µM) | Inhibition of T24 cell growth $IC_{50}$ (µM) |
|---|---|---|
| 1) | 0.22 | 7.5 |
| 3) |  | 11 |
| 6) | 0.083 |  |
| 7) | 0.023 | 4.9 |
| 8) | 0.02 | 4.15 |
| 9) | 0.053 |  |
| 10) | 0.47 |  |

What is claimed is:

1. A compound of the formula I

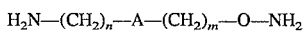 (I)

in which
the radical A is $C_3$–$C_6$cycloalkylene;
n is 0 or 1 and, independently thereof,
m is 0 or 1;
with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, or a salt thereof.

2. A compound of the formula I according to claim 1, in which
the radical A is $C_3$–$C_6$cycloalkylene;
n is 0 and,
m is 0 or 1;
with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, or a salt thereof.

3. A compound of the formula I according to claim 1, in which
the radical A is $C_3$–$C_6$cycloalkylene;
n is 0 and
m is 0;
with the provisos that a) the distance between the aminooxy radical $H_2N$—O— and the amino group —$NH_2$ is at least 3 and not more than 4 carbon atoms and that b) the two radicals $H_2N$—$(CH_2)_n$— and —$(CH_2)_m$—O—$NH_2$ are not bonded to the same ring carbon atom of A, or a salt thereof.

4. A compound of the formula I, in which
A is 1,2-cyclopropylene; 1,3-cyclobutylene; 1,3-cyclopentylene; or 1,3- or
1,4-cyclohexylene;
m is 0 or 1 and
n, independently of m, is 0 or 1;
with the proviso that the distance between the aminooxy radical $H_2N$—O— and the amino group —$NH_2$ is at least 3 and not more than 4 carbon atoms; or a salt thereof.

5. A compound of the formula I according to claim 1, in which
A is 1,2-cyclopropylene; 1,3-cyclobutylene; 1,3-cyclopentylene; or 1,3- or 1,4-cyclohexylene;
m is 0 or 1 and
n, independently of m, is 0 or 1;
with the provisos that a) the distance between the aminooxy radical $H_2N$—O— and the amino group —$NH_2$ is at least 3 and not more than 4 carbon atoms, b) n is 0 or 1 if A is 1,2-cyclopropylene or 1,3-cyclobutylene, and c) n is 0 if A is as defined other than 1,2-cyclopropylene or 1,3-cyclobutylene; or a salt thereof.

6. A compound of the formula I according to claim 1, in which
A is 1,2-cyclopropylene; 1,3-cyclobutylene; 1,3-cyclopentylene; or 1,3- or
1,4-cyclohexylene;
n is 0 and
m is 0 or 1;
with the proviso that the distance between the aminooxy radical $H_2N$—O— and the amino group —$NH_2$ is at least 3 and not more than 4 carbon atoms; or a salt thereof.

7. A compound of the formula I according to claim 1 which is in the cis or trans form, or a salt thereof.

8. A compound of the formula I according to claim 1, in which
A is 1,4-cyclohexylene,
n is 0 and
m is 0,
and which is in the cis or trans form, or a salt thereof.

9. A compound of the formula I according to claim 1, in which
A is 1,3-cyclobutylene,
n is 0 and
m is 0 or 1,
and which is in the cis or trans form, or a salt thereof.

10. A compound of the formula I according to either of claim 9, which is in the trans form, or a salt thereof.

11. A compound of the formula I according to claim 1, in which
A is 1,2-cyclopropylene,
n is 0 or 1 and
m is 1,
and which is in the cis or trans form, or a salt thereof.

12. A compound of the formula I according to claim 11 which is in the cis form, or a salt thereof.

13. trans-4-Aminooxy-cyclohexylamine of the formula I according to claim 1, or a pharmaceutically acceptable salt thereof.

14. cis-4-Aminooxy-cyclohexylamine of the formula I according to claim 1, or a pharmaceutically acceptable salt thereof.

15. trans-3-Aminooxy-cyclohexylamine of the formula I according to claim 1, or a pharmaceutically acceptable salt thereof.

16. cis-3-Aminooxy-cyclohexylamine of the formula I according to claim 1, or a pharmaceutically acceptable salt thereof.

17. cis-3-Aminooxymethyl-cyclopentylamine of the formula I according to claim 1, or a pharmaceutically acceptable salt thereof.

18. cis-3-Aminooxymethyl-cyclobutylamine of the formula I according to claim 1, or a pharmaceutically acceptable salt thereof.

19. 3-Aminooxymethyl-cyclobutylamine of the formula I according to claim 1, or a pharmaceutically acceptable salt thereof.

20. trans-3-Aminooxymethyl-cyclobutylamine of the formula I according to claim 1, or a pharmaceutically acceptable salt thereof.

21. 3-Aminooxy-cyclobutylmethylamine of the formula I according to claim 1, or a pharmaceutically acceptable salt thereof.

22. cis-2-Aminooxymethyl-cyclopropylmethylamine of the formula I according to claim 1, or a pharmaceutically acceptable salt thereof.

23. trans-2-Aminooxymethyl-cyclopropylmethylamine of the formula I according to claim 1, or a pharmaceutically acceptable salt thereof.

24. A pharmaceutical composition for the treatment or prophylaxis of a disease in warm-blooded animals which responds to inhibition of ornithine decarboxylase, which comprises an amount of a compound of the formula I according to claim 1 or of a pharmaceutically acceptable salt thereof according to claim 1 which is active against diseases which respond to inhibition of ornithine decarboxylase, together with a pharmaceutically acceptable carrier.

25. A method for the treatment of a disease which is treatable by inhibition of ornithine decarboxylase, which comprises administration of a prophylactically or therapeutically active ornithine decarboxylase-inhibiting amount of a compound of the formula I or of a pharmaceutically acceptable salt thereof according to claim 1 to a warm-blooded animal requiring such treatment.

* * * * *